(12) United States Patent
Bottesch

(10) Patent No.: US 9,539,279 B2
(45) Date of Patent: Jan. 10, 2017

(54) SYSTEM FOR IMPROVING SAFETY AND EFFICACY IN THE PREPARATION OF AN INJECTION SITE

(71) Applicant: Hans Werner Bottesch, Danville, PA (US)

(72) Inventor: Hans Werner Bottesch, Danville, PA (US)

( * ) Notice: Subject to any disclaimer, the term of this patent is extended or adjusted under 35 U.S.C. 154(b) by 37 days.

(21) Appl. No.: 13/960,450

(22) Filed: Aug. 8, 2013

(65) Prior Publication Data

US 2015/0044301 A1  Feb. 12, 2015

(51) Int. Cl.

| | |
|---|---|
| *A01N 59/08* | (2006.01) |
| *A61K 31/722* | (2006.01) |
| *A61K 45/06* | (2006.01) |
| *A61K 31/155* | (2006.01) |
| *A61K 9/00* | (2006.01) |
| *A61K 47/02* | (2006.01) |
| *A61K 47/36* | (2006.01) |

(52) U.S. Cl.
CPC ........... *A61K 31/722* (2013.01); *A61K 9/0019* (2013.01); *A61K 31/155* (2013.01); *A61K 45/06* (2013.01); *A61K 47/02* (2013.01); *A61K 47/36* (2013.01)

(58) Field of Classification Search
CPC ........ A61K 8/00; A61K 2800/43; A61Q 1/02; A61Q 1/025; A61Q 1/04; A61Q 1/06; A61Q 1/08; A61Q 1/10; A61Q 19/001; A61Q 19/02; A61Q 19/04
See application file for complete search history.

(56) References Cited

U.S. PATENT DOCUMENTS

| | | |
|---|---|---|
| 4,616,644 A | 10/1986 | Saferstein et al. |
| 4,838,854 A | 6/1989 | Kuzmanovich et al. |
| 6,267,976 B1 | 7/2001 | Barnhart et al. |
| 6,762,336 B1 | 7/2004 | MacPhee et al. |
| 8,193,325 B2 | 6/2012 | Chou et al. |
| 8,231,893 B2 | 7/2012 | Carlucci et al. |
| 8,236,781 B2 | 8/2012 | Laugier et al. |
| 8,269,058 B2 | 9/2012 | Mc Carthy et al. |
| 8,304,595 B2 | 11/2012 | Daniels et al. |

*Primary Examiner* — Hasan Ahmed
(74) *Attorney, Agent, or Firm* — Patrick J. Halloran

(57) ABSTRACT

A system is disclosed for preparing a hypodermic injection site comprising a visibility enhancer for an injection site and a post injection hypodermic puncture wound site. The present invention offers a number of significant improvements which advance the efficacy of the art, by: preventing unintentional hypodermic injection of medicines through unsanitized or under-sanitized skin surfaces, thereby protecting patients from becoming inoculated with pathogenic microorganisms while receiving such injections; significantly improving the visibility of, and, the accurate visual location and bandaging of post-injection needle puncture entry wounds, thereby further reducing the risk of infection of such wounds; and, by reducing bleeding from such wounds, which, in turn, reduces healthcare worker exposure to blood-borne pathogens and reduces the generation of potentially infectious, biohazardous medical waste.

2 Claims, 5 Drawing Sheets left panel inner aspect    right panel inner aspect adsorbent fabric patch

Transparent View of Assembled
and Sealed Components
of FIGS. 2. and 3.

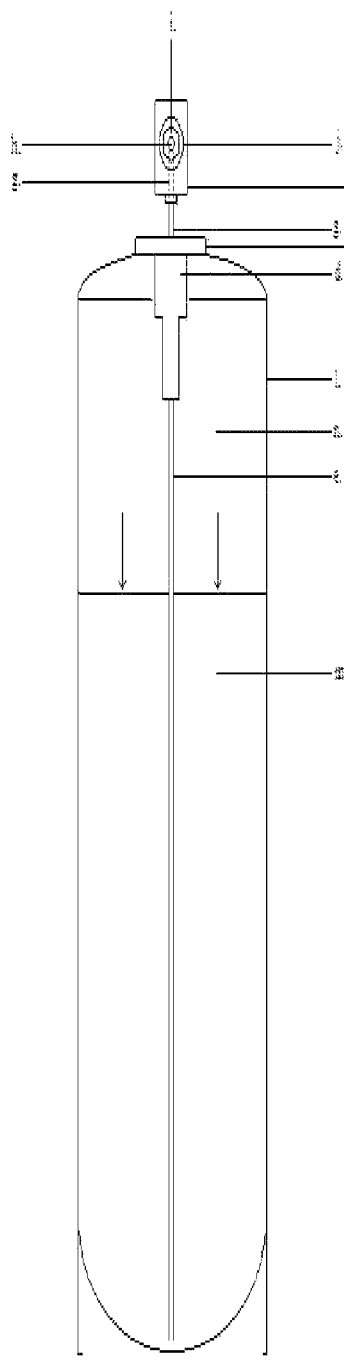
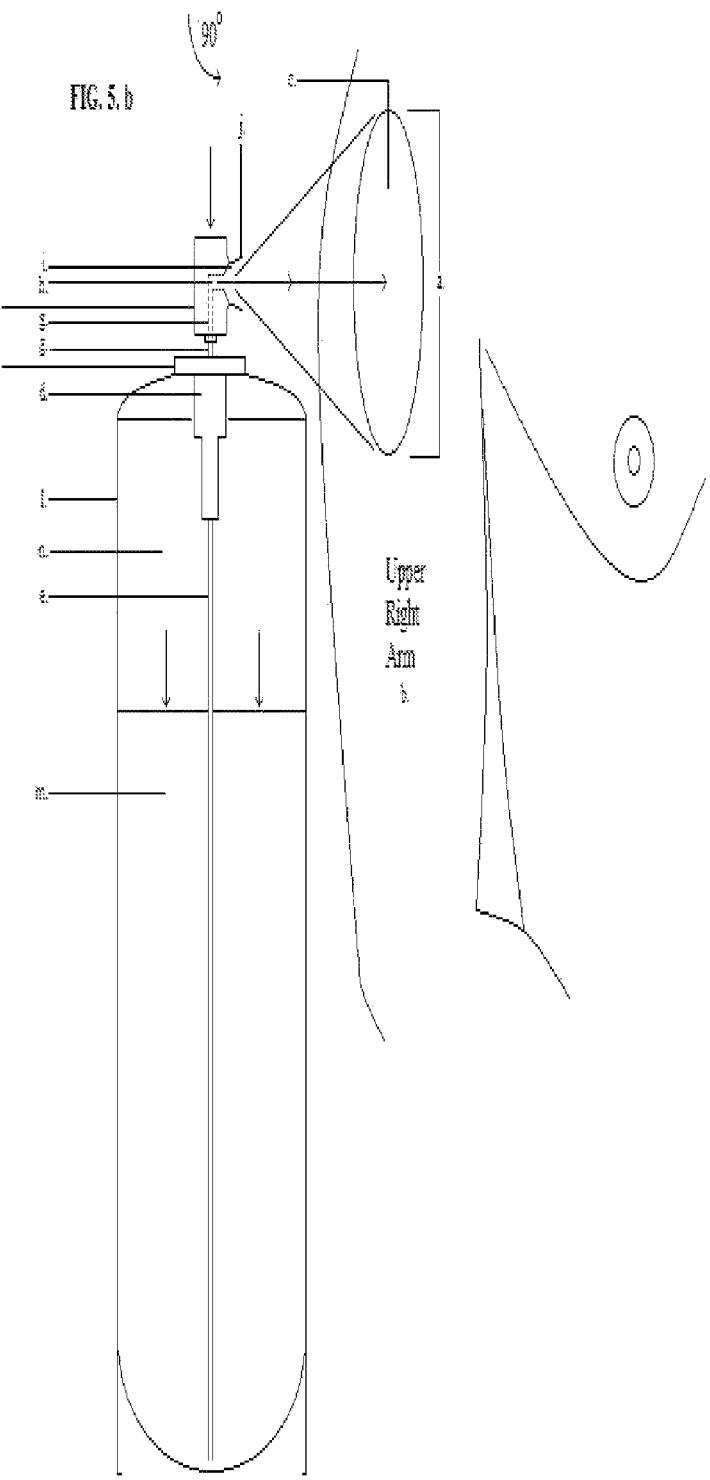
FIG. 5.a CROSS SECTION FRONTAL ASPECT
FIG. 5.b CROSS SECTION SIDE ASPECT

SYSTEM FOR IMPROVING SAFETY AND EFFICACY IN THE PREPARATION OF AN INJECTION SITE

CROSS REFERENCE TO RELATED APPLICATIONS

BACKGROUND OF THE INVENTION

A. Field of the Invention

This invention relates, in general, to volatile skin sanitizing/sterilizing agents, such as isopropyl alcohol, which are commonly applied to patients' skin surfaces by licensed healthcare professionals and by patients themselves, in order to render such skin surfaces medically safe for the hypodermic administration of injectable medicines. These agents are typically applied to skin surfaces in preparation for the administration of injectable medicines such as vaccines and antibiotics, and in preparation for the self-administration of medicines by patients such as those who self-administer insulin.

The present invention relates, in particular, to the incorporation of one or more non-volatile ingredients into such volatile skin sanitizing/sterilizing agents, thereby enabling such ingredient-enhanced agents to form a uniformly-deposited, post-evaporation layer or coating comprised of the said non-volatile ingredients, on the skin surfaces of the hypodermic injection sites to which the said ingredient-enhanced agents are applied. The present invention offers significantly improved efficacy in comparison to the skin sanitizing/sterilizing agents of the relevant prior art, by virtue of the attributes of the said non-volatile ingredients comprising its said thin, deposited layer or coating.

It is medically obvious that the injection of medicines through any un-sanitized areas of skin always presents the substantial risk of inoculating patients with pathogenic microorganisms and microscopic parasites which may reside in the local environment and/or on patients' skin surfaces at such injection site areas. Such microorganisms have the potential to cause very serious, long-term, debilitating, and even life-threatening systemic infections, especially when introduced in such a direct manner. If some patients are inadvertently inoculated with microorganisms which cause communicable diseases, the spread of such diseases through a population can be significantly accelerated.

In stark contrast to the present invention, the skin sanitizing/sterilizing agents which are disclosed in relevant prior art, when applied to a hypodermic injection site, may unwittingly be unevenly and/or incompletely applied thereto, thereby potentially forming undetectable, inadequately sanitized/sterilized gaps within the skin injection site areas treated with such antiquated agents. This increases the potential for the inadvertent injection of medicines through such undetectable gaps, which significantly increases patients' risk of being systemically inoculated with infectious microorganisms.

Prior art discloses so-called "alcohol wipes" or "alcohol swabs" which are saturated with 70% isopropyl alcohol, or, which may be saturated with one or more other, functionally similar, skin sanitizing/sterilizing agents. The said "alcohol wipes" or "alcohol swabs" are currently the most common and widely used means for skin injection site preparation. Skin sanitizing/sterilizing agents of the prior art, such as 70% isopropyl alcohol, are clear and evaporate without a trace almost immediately after their application to a hypodermic injection site. This makes it difficult, if not impossible, for an administrator of injectable medicines to identify the boundaries of, and to verify the continuity-of-sanitization of the treated site of injection, because the sanitizing/sterilizing reagent has evaporated without a trace and may or may not have been uniformly applied to the injection site prior to the injection of such medicines. Under such circumstances, hypodermic injections may also be inadvertently given through completely untreated areas of skin lying outside of the treated skin areas. This is medically unsafe and unacceptable.

The present invention discloses means for ensuring the continuity-of-sanitization at pre-treated skin injection sites, this being of prime medical importance, because when such sites are treated with the said sanitizing/sterilizing solution/suspension/slurry comprising the present invention, the presence of the said thin, deposited layer or coating prevents any un-sanitized or under-sanitized gaps from escaping visual detection within the confines of such treated skin injection site areas. Use of the present invention prevents the administrators of injectable medicines from unintentionally administering injections through undetected, un-sanitized or under-sanitized gaps which can occur within such treated skin injection site areas, and ensures that such injections are given only through uniformly sanitized/sterilized skin injection site areas. One or more blood coagulants are included in the said sanitizing/sterilizing solution/suspension/slurry comprising the present invention and are deposited as a component of the said thin, deposited layer or coating, in order to: enhance the visibility of hypodermic needle puncture entry wounds; reduce bleeding from such puncture wounds; and, to reduce the generation of infectious medical waste associated with the administration of such injections.

The present invention resolves the very serious medical inadequacies inherent in the use of the antiquated means disclosed in the prior art, by enabling the administrators of injectable medicines to visually locate and identify such treated skin injection site areas with the naked eye, and to qualitatively evaluate them for their continuity-of-sanitization.

This is accomplished by their visual examination of the uniformity of the coloration of the said thin, deposited layer or coating, for either the absence of, or the presence of any untreated or under-treated gaps within the boundary of the said deposited layer or coating. The absence of such gaps indicates that such an injection site has been uniformly sanitized/sterilized, and that an injection may be safely administered through the said deposited layer at such an injection site. The presence of one or more such gaps indicates that: the said injection site was inadequately prepared and has not been uniformly sanitized/sterilized; and, that it must therefore be re-treated and visually re-evaluated before an injection can be safely administered through that injection site. If such gaps are detected, the pigment/tint/dye/colorant-enhanced, body-fluid-reactive, blood coagulant-enhanced, skin injection site sanitizing/sterilizing solution/suspension/slurry of the present invention is easily re-applied until the said deposited layer becomes uniform in its consistency and coloration, thereby ensuring: the continuity-of-sanitization at the said injection site; the uniformity of the said deposited layer; and, the safe injection of medicines through such a uniformly sanitized/sterilized skin injection site area. This enables the administrators of injectable medicines to significantly reduce their patients' risk of acquiring potentially serious infections consequent to the administration of injectable medicines, thereby improving both the safety of administering hypodermic injections and the overall quality of their patients' health.

The exclusive and widespread use of the pigment/tint/ dye/colorant-enhanced, body-fluid-reactive, blood coagulant-enhanced, skin injection site sanitizing/sterilizing solution/suspension/slurry comprising the present invention will ensure continuity-of-sanitization at skin injection site areas for all patients receiving hypodermic injections, and will greatly decrease their risk of inadvertently acquiring local and/or systemic infections as a consequence of receiving injectable medicines. The reduction of this risk is highly significant when seen in the context of the many millions of injections and immunizations which are administered annually on a global scale, and the importance of potentially reducing this risk on such a grand scale is exponentially magnified. This is especially true for injections and immunizations which are administered in the field, in remote, rural locations where sanitation is limited or non-existent, both here and abroad.

In one or more of the preferred embodiments of the present invention described below, at least two means are disclosed for precisely locating the entrance wound opening of a post-injection needle puncture wound, even when only miniscule oozing of blood and body fluids occurs. One of these means involves the physical and/or chemical reactions which occur when the said pigment/tint/dye component comprising the said thin, deposited layer or coating becomes progressively exposed to the blood/body fluids as they progressively ooze from the post-injection, needle puncture wound entrance. As the said layer or coating adjacent to the said wound entrance becomes progressively exposed to the said oozing blood/body fluids, it becomes progressively discolored, thereby forming a highly visible, progressively-expanding ring of discoloration which encircles, and identifies the location of, the said wound entrance. Another of these means involves the further enhancement of post-injection, needle puncture wound visibility via blood clot formation at the said needle puncture wound's surface opening. Blood clotting at the said needle puncture wound entrance is induced by the blood coagulant ingredient present in the said deposited layer or coating. As the said layer or coating adjacent to the said wound entrance becomes progressively exposed to the said oozing blood/body fluids, its blood coagulant ingredient also becomes progressively exposed to the said oozing blood/body fluids, thereby initiating blood clot formation at the said needle puncture wound entrance. The coloration and physical appearance of the blood clot thus formed, demarcates the said needle puncture wound entrance in and of itself, and its visible presence simultaneously contributes to the visibility and location of the said wound entrance as stated in the previously-cited means.

The present invention improves on the art by preventing the proliferation of diseases acquired as an unintended consequence of receiving injectable medicines and vaccines, and as an unintended consequence of accidental exposure to infectious medical waste associated with excessive injection site bleeding.

A. Description of the Related Art

U.S. Pat. No. 8,269,058; McCarthy, et al.; The authors disclose an absorbable tissue dressing assembly having a sponge-like, chitosan matrix structure and a woven nano-fiber and/or micro-fiber backing material, possessing different colors, "to facilitate identification by a caregiver". Patches of this dressing assembly are applied internally to achieve hemostasis during surgical operations. Clot formation is achieved by the attraction of the negatively charged red blood cell membranes to the positively-charged surface of the chitosan matrix. In the present invention, blood clot formation also occurs at post-injection hypodermic needle puncture wounds, both by muco-adhesive adsorption of the oozing red blood cells by the chitosan in the said deposited layer, and by physiologically-related clotting mechanisms. However, the present invention utilizes such clot formation to visually identify and locate the said needle puncture wound to facilitate its accurate bandaging. The McCarthy, et al. disclosure does not cite, contemplate or anticipate the utilization of clotting as means to locate a post-injection hypodermic needle puncture wound, and no reference of any kind is made in the authors' text or claims pertaining to any aspect of the present invention.

U.S. Pat. No. 8,236,781, Laugier, et al.; The authors disclose a hydrogel comprised of chitosan carboxyalkylamide, several forms of which are applied into or (as a protective coating) onto burn wounds of varying degrees of severity. The pH of their chitosan variant is adjusted to approximate the pH of human skin, yet is capable of gel formation and works equally well in a dried form when directly applied onto or into such burn wounds. The addition of "colorants" to the authors' chitosan variant is cited only once, at the bottom of their page 7, in brief reference which does not disclose purpose, nor is the use of "colorants" cited in their claims. No other reference of any kind is made in the authors' text or claims pertaining to any aspect of the present invention. The Laugier, et al. disclosure does not cite or contemplate their chitosan variant's ability to: coagulate blood at a wound site; physically and/or chemically react with the blood/body fluids which ooze from hypodermic needle puncture wounds in order to produce a visually-detectable localized color change at the surface opening of such wounds; or, to mask local skin blemishes (such as freckles) existing beneath a prepared hypodermic injection site in order to facilitate the identification, location and proper bandaging of post-injection hypodermic needle puncture wounds. Laugier, et al. also disclose a hydrogel comprised of chitosan carboxyalkylamide which is dehydrated to form a powder. This form of chitosan is included by reference, as an ingredient in at least one of the said non-volatile components comprising the present invention.

U.S. Pat. No. 8,231,893; Carlucci, et al.; The authors disclose a chitosan variant which is utilized to coat an inert, particulate carrier material, which in turn, is then "incorporated into an absorbent structure", such as a disposable diaper or wipe. This coated article performs absorption of liquids and is not involved in transferring chitosan onto a secondary surface, such as a hypodermic skin injection site. No reference of any kind is made in the authors' text or claims pertaining to any aspect of the present invention. Carlucci's chitosan-coated material is cited as performing gelification and absorption of blood and menses, rather than augmenting natural clot formation at a hypodermic needle puncture wound site, thereby further distinguishing Carlucci from the present invention. Carlucci, et al.,'s use of chitosan does not involve inherent physiological clotting mechanisms. The altered form(s) of chitosan disclosed by Carlucci, et al., is not cited as possessing any coagulative properties, and such coagulative properties are not represented in their disclosure.

U.S. Pat. No. 8,304,595; Daniels, et al.; Nov. 6, 2012; The authors recite the formulation of nanostructures comprised of various materials such as chitosan microparticles which are used to coat a variety of substrate materials in order to provide enhanced hemostasis for bandages, etc. These coated substrate materials are applied to various wounds to induce improved hemostasis. The authors do not disclose the use of their substrate materials as means to transfer their coagulant materials from their substrate materials to a secondary surface, such as a skin hypodermic injection site.

U.S. Pat. No. 6,762,336, MacPhee, et al.; disclose a hemostatic sandwich bandage for application to a variety of wounds, including external skin wounds. The authors do not disclose the use of their bandage as means to transfer their coagulant materials to a secondary surface, such as a skin hypodermic injection site.

U.S. Pat. No. 4,616,644, Saferstein, et al.; The authors disclose an adhesive bandage having a coating of polyethylene oxide which reacts with blood proteins: prothrombin and plasma fibrinogen to increase the rate of hemostasis at a wound site. The authors do not disclose the use of their bandage as means to transfer their coagulant materials to a secondary surface, such as a skin hypodermic injection site.

U.S. Pat. No. 6,267,976; Barnhart, et al.; 424/401, 514/844; In reference to surfactant cleaners of the prior art, Barnhart states, in his "BACKGROUND OF THE INVENTION", that "dyes were needed in the in the surface cleaner to visually determine and insure that a particular surface had been contacted by the cleaner and disinfectant." He states that "U.S. Pat. Nos. 4,965,063, 5,110,492, 5,057,303, and 5,064,635 all describe overcoming this problem by providing a cleaning composition for surfaces having a pH sensitive dye which includes a germicide and disappears upon exposure to air", and that "such a pH sensitive dye might be useful in a surface cleanser, it is not particularly useful in a skin cleansing composition" "since the dye would disappear before it was dispensed." He further states that "if the user did not remove all of the cleaner from the surface however, a colored residue would still remain." Barnhart also states that photosensitive dyes "have commonly been used to determine whether a product has been exposed to light so as to warn the user of a particular hazard." In his "PREFERRED EMBODIMENT FOR CARRYING OUT THE INVENTION" Barnhart specifically states that "Dyes of the type utilized in the skin cleansing compositions of the present invention are added essentially for the aesthetic effect they create in producing a colored product, not for any cleansing properties associated therewith." Clearly, Barnhart's inclusion of such dyes is not intended for use in the demarcation of a site on the skin intended for the injection of a medicine or vaccine, as is the case in the present invention, nor is any suggestion for such usage mentioned in his text. Photosensitive dyes such as those which are cited as examples in Barnhart, specifically D&C Red No. 28 and Blue No. 1, may be suitable as skin demarcation agents in the present invention, owing to their unique properties as cited in Barnhart. The thin layering of dye utilized in the present invention can also considerably reduce the time intervals required for photo decolorization to take place as opposed to those times cited in Barnhart under his "TABLE II COLOR FADING PROPERTIES OF SAMPLE COMPOSITIONS" section. Barnhart states that non-photosensitive dyes may also be used.

U.S. Pat. No. 4,838,854; Kuzmanovich; 604/506; 604/116, pertains to marking the skin with a non-sterile "opaque" liquid and then "sterilizing" the skin area prior to injection. Kuzmanovich does not disclose any physical and.or chemical reactions taking place between his marking substance and the blood/body fluids which ooze from a hypodermic needle puncture wound. The use of the term "sterilization" is incorrect, since sterility of injection sites cannot be guaranteed, and since some organisms are not affected by the agents used for such "sterilization", and can therefore be introduced sub-dermally during an injection. The container harboring the said "opaque" liquid is unsanitary, and can become increasingly contaminated by micro organisms after repeated use, thus making this device hazardous to the public health. The application of a dot of the "opaque" liquid does not enable the person giving the injection to accurately determine whether or not the entire affected area of skin has been completely sanitized.

U.S. Pat. No. 8,193,325; Chou, et al.; The authors disclose a processing method for producing nano-particulate chitosan for use in medical applications and other uses. Although Chou, et al. disclose their "nano-miniaturized chitosan" as being "blended to develop antiseptic wound dressing and novel textile as well as cosmetological products such as fiber, non-woven, medical dressing, dress, fabric, cosmetic skin mask and the like, wherein the molecular weight of said nano-miniaturized chitosan is less than 50 k.", and further, that this form of chitosan is "being further introduced into the fiber manufacturing process with Dry-jet Wet Spinning method to manufacture desired fiber fabric having features of enhanced antiseptic, moisture-retentive and deodorizing capabilities", Chou, et al. do not contemplate, disclose, or claim simple adsorption onto their fabric surface for purposes of topical application to, and visual demarcation of skin injection sites. One of Chou's cited references pertains to the "Decolorization of Chitosan by Ozone Treatment" (first reference listed), which is not a desirable attribute within the context of the present invention. In passing, Chou, et al. do refer to the use of their form of chitosan as a "cosmetic skin mask", but this has no relevance in relation to the visual demarcation of skin injection sites, or in relation to the masking of skin blemishes (such as freckles), to prevent the visual occlusion of hypodermic needle puncture wound openings. Curiously, Chou, et al. do not claim the property of coagulation for their form of chitosan, per se., perhaps because this property may have been diminished by their processes. No reference of any kind is made in the author's text or claims pertaining to any aspect of hypodermic injection site preparation.

International Patent Number: AT499923 (T); (issued Mar. 15, 2011), Stengele, et al., International Classification: A01N31/02; A61K8/34; 8/365; 8/46; 8/49; 8/81, A61Q17/00; European Classification: A61K8/34; 8/365; 8/46F, 8/49C6; 8/81R2, A61Q17/00F; and A01N31/02, "Antiseptic Skin Dye"; For additional reference, this patent is also internationally published as patent numbers: DE102007030416 (A1), EP2011475 (A2, A3, and B1), and as ES2361587 (T3).

Stengele, et al. cite on page 9, that: "The invention is suitable for coloring skin colorants, small and large areas of skin before a surgical or medical treatment, such as before surgery, an injection or a puncture". "The staining solutions used here may have a disinfecting effect and additional staining of the skin by the medical staff it is possible to make sure that the entire area was disinfected". Stengele, et al. can clearly be used to demarcate and disinfect a small patch of skin prior to an injection, but its composition is needlessly complex and expensive to mass produce in a form suitable specifically for that purpose. However, their invention does not disclose, nor does it contemplate the use of coagulants in association with the demarcation and disinfection of hypodermic injection sites, or the preparation of skin sites for surgery.

The authors further state that the solution comprising their invention requires at least one additional application in order "to make sure that the entire area was disinfected". Complete "disinfection", amounting to sterilization of such a skin area is not fully attainable using such means. At best, a reasonable sanitization of the area can be achieved using such means. Furthermore, Stengele, et al. do not disclose the use of such colorants as means to enable the administrator of such injections to better distinguish an injection puncture wound from surrounding skin blemishes (such as freckles), especially when there is no visible post-injection bleeding or oozing at the injection wound site, as is often the case during the administration of intramuscular and subcutaneous injections. In addition to the initial demarcation and sanitization of a patient's injection site as offered in Stengele, et al., the present invention additionally improves the visibility of post-injection puncture wounds, thereby allowing for more accurate location and bandaging of such puncture wounds, which in turn reduces the potential for later infection of such wounds, and thereby improves the overall health of such patients. Also, Stengele, et al. does not mention or contemplate the coagulation of blood oozing from a needle puncture wound as a means for making such puncture wounds easier to identify and accurately bandage. Stengele, et al. claims the use of triarylmethane dyes, indigo dyes, xanthine dyes, quinophthalone, anthraquinone dyes, quinoline yellow (E104), patent blue V (E131) and or brilliant green BS (E142).

In contrast to the prior art, the present invention offers a number of significant improvements which advance the efficacy of the art, by: preventing unintentional hypodermic injection of medicines through un-sanitized or under-sanitized skin surfaces, thereby protecting patients from becoming inoculated with pathogenic organisms while receiving such injections; significantly improving the visibility of, and, the accurate visual location and bandaging of post-injection needle puncture wounds, thereby further reducing the risk of infection of such wounds; and, by reducing bleeding from such wounds, which, in turn, reduces healthcare worker exposure to blood-borne pathogens and reduces the generation of potentially infectious, biohazardous medical waste.

SUMMARY OF THE INVENTION

The present invention relates to a system for preparing a hypodermic injection site comprising:
  a. at least one visibility enhancer for an injection site and a post injection hypodermic puncture wound site.

The present invention further relates to a system for preparing a hypodermic injection site comprising:
  a. at least one visibility enhancer for an injection site and a post injection hypodermic puncture wound site; and
  b. at least one injection site sanitizer.

The present invention also relates to a system for preparing a hypodermic injection site comprising:
  a. at least one visibility enhancer for an injection site and a post injection hypodermic puncture wound site; and;
  b. at least one injection site sanitizer; and
  c. at least one injection site coagulant.

DEFINITIONS AND USAGES OF TERMS

Within the context of the present disclosure, the following terms:

SUSPENSIONS, SLURRIES AND SOLUTIONS: are each defined as being comprised of a combination of VOLATILE and NON VOLATILE COMPONENTS which are further defined below; the compositions of each of which are comprised of varied ingredients in various proportions to one another, as disclosed herein, in their respective specifications. The commonly accepted definitions of these terms apply in relation to their usage in the context of the present invention, with the exception that the definition of the term SLURRY is herein broadened from its commonly accepted definition, and is defined as being comprised of a microscopically-ground, grit-free mixture of the ingredients comprising the said "non-volatile component", which is moistened with a sufficient volume of the said "volatile component" via mechanical grinding or other means, thereby formulating a semi-fluid composition which is comprised of the said mixture of the said VOLATILE COMPONENT and the said NON VOLATILE COMPONENT.

VOLATILE COMPONENT: is defined as comprising: any aqueous-based liquid such as a solution of chlorhexidine gluconate, sodium hypochlorite, or benzalkonium chloride; any organic-based liquid such as an alcohol, or any combination thereof, in which may be dissolved or suspended, one or more skin sanitizing agents such as chlorhexidine gluconate, any combinations of which: are medically safe for application to human skin surfaces; are capable of sanitizing such skin surfaces by attenuating or killing most pathogenic microorganisms, such as bacteria, viruses and parasites residing on such skin surfaces; are capable of functioning as a vehicle for physically transferring the sub-component ingredients comprising the NON VOLATILE COMPONENT onto such skin surfaces; and, are capable of rapidly evaporating from such skin surfaces, thereby depositing the ingredients comprising the NON VOLATILE COMPONENT onto such skin surfaces. In the context of the present invention, the VOLATILE COMPONENT functions as both a SKIN SANITIZER and as vehicle for physically transferring the NON VOLATILE COMPONENT onto the skin surface at a selected injection site.

NON VOLATILE COMPONENT: is defined as comprising one or more individual, multi-functional, non-liquid, non-evaporative, sub-component chemical ingredients, which are selected from diverse categories of chemically unrelated substances, based on specific physical and/or chemical attributes which enable them to perform in accordance with the invention's specifications, by forming thinly and uniformly-deposited layers at selected injection sites, which enhance both injection site visibility, and injection wound site visibility by physically, and/or chemically, and/or physiologically reacting with the blood/body fluids oozing from such wounds, thereby producing visible discoloration of the area of the said deposited layer adjacent to such wounds, while also enhancing coagulation at such wound sites. Non-limiting examples of such unrelated chemical substances include: micro-particulate Titanium Dioxide (an inorganic substance), and Chitosan in one or more of its useable forms (a polysaccharide). In the context of the present invention, the NON VOLATILE COMPONENT is comprised of one or more substances which are capable of forming thinly DEPOSITED LAYERS on selected injection sites, the constituent ingredients of which may function as VISIBILITY ENHANCERS and/or COAGULANTS as defined herein.

DEPOSITED LAYER: is defined as the coating comprised of the sub-component ingredients of the said NON VOLATILE COMPONENT, which remains on the skin surface at a selected injection site treated with one of the SUSPENSIONS, SLURRIES OR SOLUTIONS comprising the present invention, resulting from the evaporation of the said VOLATILE COMPONENT from the said treated skin injection site.

VISIBILITY ENHANCER: is defined as one or more of those sub-component ingredients comprising the said NON VOLATILE COMPONENT, which physically, and/or chemically, and/or physiologically react with the blood/body fluids oozing from the said post-injection needle puncture wounds, thereby causing visible changes in the coloration of the said DEPOSITED LAYER in the area adjacent to and surrounding the said puncture wounds. In the context of the present invention, a substance which functions as a VISIBILITY ENHANCER may also function independently as a COAGULANT as defined herein.

SKIN SANITIZER: is defined as describing one of the functional aspects of the VOLATILE COMPONENT of the present invention, the ingredients of which, when topically applied to a selected skin injection site, enable it to attenuate or kill most of the pathogenic microorganisms, such as bacteria, viruses, and parasites residing on such human skin surfaces.

COAGULANT: is defined as comprising one or more of the sub-component ingredients of the said NON VOLATILE COMPONENT, which will induce clotting, regardless of the mechanism by which clotting is achieved, such as by: triggering the natural physiological clotting processes following the withdrawal of the needle from the skin; by simple adsorption of the said oozing blood/body fluids onto Titanium Dioxide's particle surfaces; and/or, by muco-adhesion of the said oozing blood/body fluids to Chitosan. In the context of the present invention, a substance which functions as a COAGULANT may also function independently as a VISIBILITY ENHANCER as defined herein.

Within the context of the present invention, the terms APPLIED and DEPOSITED are utilized in keeping with the distinction that the term "APPLIED" refers to the physical application of the combined volatile and non-volatile components comprising the present invention to a skin surface injection site, while the term "DEPOSITED" refers only to the sub-component ingredients comprising the said NON VOLATILE COMPONENT which remain on the skin surface of the said treated injection site, following the evaporation of the said VOLATILE COMPONENT therefrom.

BRIEF DESCRIPTION OF THE DRAWINGS

FIGS. 5.a. and 5.b. illustrate cross sectional views of an aerosol container and dispensing device for applying the solutions/suspensions comprising the sixth embodiment of the present invention to a human skin surface, specifically, an illustration of the application of the invention to an injection site on the skin covering the deltoid muscle of a human being's upper right arm. FIG. 5.a. depicts a cross sectional view of the said container and device from a frontal aspect, while FIG. 5.b. illustrates the container of FIG. 5.a. which has been rotated 90 degrees counterclockwise on its vertical axis.

DETAILED DESCRIPTION OF THE INVENTION

Figure 1:
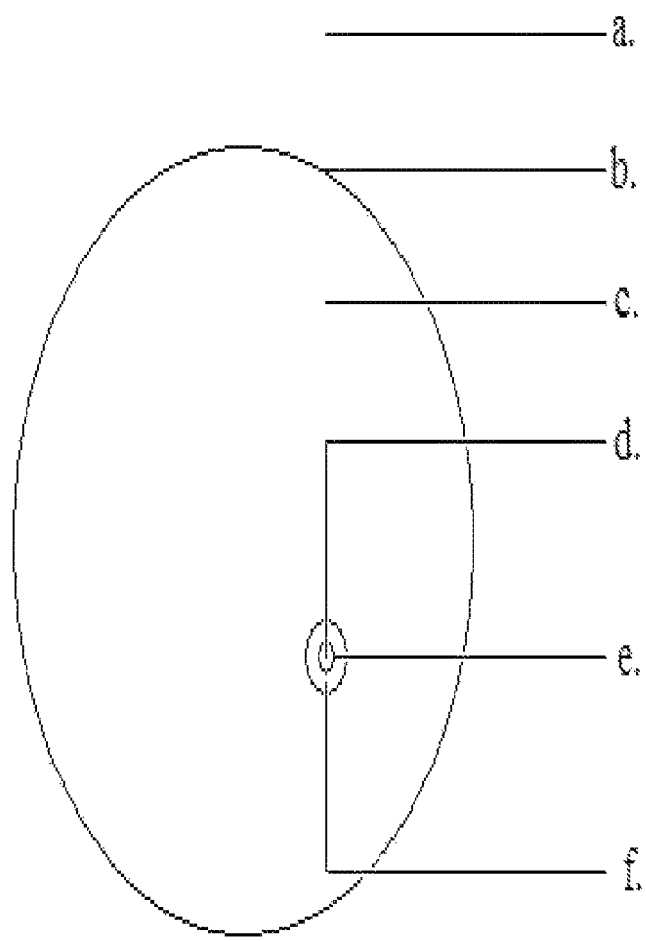
FIG. 1 illustrates an un-sanitized, exposed area of human skin, "a.", to which the solution/suspension/slurry comprising the present invention has been applied at skin injection site area, "c.", via the disposable, adsorbent fabric or sponge-like patch, swab, or wipe, "f." of FIG. 4, thereby sanitizing/sterilizing skin area "c.", while visually demarcating it from the said un-sanitized, untreated area of human skin, "a.".

The present invention relates to a system for preparing a hypodermic injection site comprising:
  a. at least one visibility enhancer for an injection site and a post injection hypodermic puncture wound site.

The present invention further relates to a system for preparing a hypodermic injection site comprising:
  a. at least one visibility enhancer for an injection site and a post injection hypodermic puncture wound site; and
  b. at least one injection site sanitizer.

The present invention also relates to a system for preparing a hypodermic injection site comprising:
  a. at least one visibility enhancer for an injection site and a post injection hypodermic puncture wound site; and;
  b. at least one injection site sanitizer; and
  c. at least one injection site coagulant.

The present invention discloses various formulations of a topically-applied, pigment/tint/dye/colorant-enhanced, body-fluid-reactive, blood coagulant-enhanced, skin injection site sanitizing/sterilizing solution/suspension/slurry, hereinafter referred to as the "solution/suspension/slurry", each such variation being comprised of an evaporative fluid or "volatile component", and a multi-ingredient, non-evaporative "non-volatile component".

It can be said that chemicals which are deemed "insoluble" in a given solvent, may still be minutely soluble on a molecular level. Similarly, chemicals which resist suspension in a given liquid, may still exhibit some minute degree of suspendability on a molecular level. Such terminology is therefore not absolute. In this context, if the ingredients comprising the said "non-volatile component" are only partially soluble and/or partially suspendable in the said "volatile component", then a reduction in the volume of the said "volatile component" may be necessary to facilitate the milling of the incompletely dissolved/suspended ingredients into a finely-ground slurry. Particle size within the said slurry is reduced to the point where tactile grittiness is undetectable. The creation and applied use of such a finely-ground slurry circumvents such solubility issues within the context of the present invention.

The evaporative fraction comprising the said "volatile component" is selected for its ability to sanitize/sterilize the injection site skin surface to which it is applied prior to the administration of an injectable medicine. The said "volatile component" functions as a vehicle for the said "non-volatile component". The multiple ingredients comprising the said "non-volatile component" are dissolved, and/or suspended in the said "volatile component", and/or are sufficiently moistened by the said "volatile component" via milling or grinding of the mixture in order to form at least a partial a slurry thereof. The said "volatile component" is comprised of an agent such as 70% isopropyl alcohol, or another evaporative agent having functionally-similar or identical properties, which may be combined with one or more additional, evaporative agents also having functionally-similar or identical properties, as defined within the context of the present invention.

One or more of the ingredient(s) comprising the said "volatile component" are selected based on the broadness of their spectrum of antimicrobial activity; the speed at which they evaporate from human skin surfaces to which they are topically applied; and, their safety for human use when topically applied, thereby optimizing their performance within the context of the present invention. The optimized formulation of the said "volatile component" is derived through empirical experimentation, utilizing means and methods which are well known and established in the art, in order to achieve optimal levels of performance for each of the said components as well as for each of the individual ingredients of which the said components are comprised.

Surfactants and/or suspending agents may be included as ingredients in either or both the "volatile components" and the "non-volatile components" comprising the various embodiments of the present invention, in order to facilitate both their admixture and their topical application to skin surfaces.

The said multi-ingredient "non-volatile component" is comprised of a mixture of physically and/or chemically-compatible sub-component ingredients which include but are not limited to: one or more known surfactants such as DSS (dioctyl sodium sulfosuccinate or docusate sodium); one or more known suspending agents (which may be required for proper admixture to occur); one or more body-fluid-reactive, fluorescent and/or non-fluorescent pigments, tints, dyes, or colorants; and, one or more blood coagulants, which are all collectively dissolved and/or suspended in, and/or slurried with the said evaporative "volatile component", thereby formulating one or more of the embodiments comprising the present invention. It is acknowledged that numerous variations of such formulations are possible, based on variations in the selection of each of the said ingredients, and on variations in the measured quantities of each of the said selected ingredients utilized in formulating the "volatile component" and/or the "non-volatile component" comprising the present invention. Such variations are set forth in the various embodiments disclosed herein, and all such possible variations are claimed as falling within the scope and intent of the present invention.

When any of the various formulations of the said "solution/suspension/slurry" comprising the present invention is applied to human skin injection site areas, the said "volatile component" sanitizes/sterilizes and rapidly evaporates from such skin areas, leaving behind the ingredients comprising the said "non-volatile component", which becomes deposited onto the surface of the skin area to which it has been applied, thereby forming a uniform, two-dimensional, post-evaporation layer or coating which is visually opaque, translucent or semi-transparent, and which has visibly demarcated boundaries which enable it to be visually distinguished from adjacent, untreated areas of skin.

One or more of the said pigments/tints/dyes/colorants, which comprise a fraction of the said non-volatile component, are utilized to impart coloration to one or more of the said thinly deposited layers or coatings, thereby enabling and augmenting the said layers' or coatings' ability to occlude or otherwise conceal or mask any skin blemishes, freckles, tattoos, or other skin markings which may reside beneath such deposited layers or coatings. In addition, the said pigments/tints/dyes/colorants physically and/or chemically react with any blood/body fluids which ooze from a post-injection, hypodermic needle puncture wound, such reactions producing localized, visually-discernable discoloration of the specific part of the said deposited layer or coating which is physically adjacent to the surface opening of such a needle puncture wound. The blood coagulant fraction of the said deposited layer or coating is selected for inclusion in one or more of the disclosed formulations, based on its ability to simultaneously initiate robust, localized clotting when exposed to the blood component of the said blood/body fluids which ooze from the said surface opening of the hypodermic needle puncture wound. The said blood coagulant fraction is, for example, comprised of at least one form of chitosan, such as: dehydrated chitosan carboxyalkylamide; dehydrated chitosan silver nitrate gel; chitosan silver complex; chitosan/silver nanocomposite; etc., etc.

The initiation of blood clot formation at the said needle puncture wound opening, serves to both increase the visibility of the said wound opening, and to decrease the flow of blood from such wounds, thereby decreasing healthcare worker exposure to blood-borne pathogens and decreasing the generation of infectious medical waste associated with bleeding from such wounds. Such deposited layers or coatings therefore serve to: occlude or partially-occlude any skin blemishes (such as freckles) residing beneath such treated skin injection site areas; make the uniformity of coloration of such deposited layers visually observable and re-treatable if necessary; physically and/or chemically react with body fluids oozing from post-injection hypodermic needle puncture wounds, thereby producing visually identifiable changes in coloration at the surface entrances of such wounds; and, initiate visible blood clot formation at such wound sites, thereby further enhancing wound visibility. Examples of body fluid components which may ooze from such needle puncture wounds in minute or larger quantities include blood, plasma, lymph fluid, cutaneously-deposited fats, sebaceous oils, or combinations thereof, etc. It is also desirable that both the said "volatile component", and the said pigment(s) or tinting agent(s) sub-component of the said "non-volatile component", comprising the present invention, are selected for their antiseptic and/or antibacterial/antiviral/antifungal properties, in order to enhance the potential for additive and/or synergistic sanitizing/sterilizing effects when combined. The same can be said for the other sub-component ingredients comprising the said "non-volatile component".

The said thinly deposited layer provides means for the immediate visual identification and location of the said treated skin injection site area and enables an administrator of hypodermic injections to visually confirm the integrity of the sanitization of such treated skin areas, by visually examining, evaluating and confirming the uniformity of the coloration of the said deposited layer (referred to herein as the "continuity-of-sanitization") prior to the administration of hypodermic injections within the boundaries of such a treated skin area. This visual examination of such treated injection sites enables the administrator of a hypodermic injection to identify and re-treat such skin areas if gaps or variations in such layer coloration are observed prior to the administration of such injections, thereby preventing the hypodermic injection of medicines through un-sanitized, untreated, or under-treated skin, which can often result in patients becoming unintentionally inoculated with pathogenic organisms which can cause post-injection cysts and other serious, life-threatening systemic infections and communicable diseases.

It is an objective of the present invention to not only enable the administrators of such injectable medicines to positively identify the outer boundaries of their patients' sanitized skin injection site areas, but to also enable them to visually confirm that the skin sanitizing/sterilizing solution which has been applied within the boundaries of such skin injection site areas has been uniformly applied, thereby preventing the occurrence of undetected, un-sanitized or under-sanitized gaps within the said boundaries of such sanitized skin injection site areas. If the skin sanitizing/sterilizing agents/solutions of the prior art are applied to a skin injection site prior to the administration of an injection, then undetectable, un-sanitized, or under-sanitized gaps could potentially occur within the said boundaries of such treated skin injection site areas, during the administrators' physical application of such skin sanitizing/sterilizing solutions to patients' skin. If the skin sanitizing/sterilizing reagents/solutions of the prior art are applied to patients' skin, any un-sanitized or under-sanitized gaps which may occur during such applications would be invisible to the administrators of such injectable medicines following their evaporation from patients' skin. The injection of medicines through such un-sanitized or under-sanitized gaps may have unintended consequences for such patients, such as the formation of post-injection cysts and the inoculation of such patients with other serious, or even fatal opportunistic infections, which may also be highly contagious in and of themselves. In addition, the treated skin area could be missed altogether during the administration of such an injection.

It is also an objective of the present invention to enable the administrators of such injectable medicines to more easily distinguish between such post-injection needle puncture wounds and the multiple, variably-toned skin blemishes, such as freckles, which are often found in close proximity to such puncture wounds. When skin sanitizing/sterilizing solutions of the prior art are utilized to pre-treat such blemished skin injection site areas, and when negligible oozing occurs from the surface openings of such post-injection needle puncture wounds, such needle puncture wounds often blend in with and become almost totally obscured by, and indistinguishable from such blemishes. In such circumstances, the administrators of injectable medicines often find it very difficult, if not impossible, to visually re-acquire the locations of such blemish-obscured needle puncture wound openings, after being visually distracted by following established immunization procedures which require them to immediately focus their attention on the safe disposal of the post-injection, patient-contaminated needles/syringes, prior to the bandaging of such wounds. In contrast to the prior art, when the skin sanitizing/sterilizing solution/suspension/slurry comprising the present invention is applied to patients' skin injection sites, it uniformly occludes any underlying skin blemishes (such as freckles) at such injection sites, thereby enabling the administrators of such medicines to more easily re-acquire the locations of such post-injection needle puncture wound openings after being visually distracted as cited above, even when little or no oozing occurs at such wound openings. This further enables the administrators of such medicines to more accurately locate and bandage such puncture wounds, which, in turn, further reduces the risk of infection of such wounds and consequently further improves the general health of patients receiving injectable medicines.

It is also an objective of the present invention to induce at least one physical and/or chemical reaction at a hypodermic injection site, between the two elements comprising: the blood and/or body fluids oozing from a post-injection needle puncture wound, and, the said ingredients comprising the said deposited layer or coating. The said reaction is initiated when physical contact occurs between the said two elements, and produces a visible discoloration of the said deposited layer or coating in the area immediately adjacent to the said wound opening, thereby creating a highly visible contrast in coloration between the area immediately adjacent to the said wound opening and the unaffected remainder of the said deposited layer or coating, thereby facilitating the accurate location and bandaging of the said wound opening, which, in turn, further reduces a patient's risk of infection at the said post-injection needle puncture wound site.

Additional objectives of the present invention include the controlling of excessive bleeding from post injection, hypodermic needle puncture wounds while simultaneously enhancing the visibility and location of such wounds following the administration of hypodermic injections. This is accomplished by including one or more blood coagulants, such as chitosan or one or more of its usable forms or derivatives, which include but are not limited to: dehydrated chitosan carboxyalkylamide; chitosan silver complex; nanoparticulate chitosan, etc.; in at least one of the formulations of the said "solution/suspension/slurry" comprising the present invention. The addition of one or more of such coagulants to one or more of the said formulations effects a reduction in the rate of bleeding at such post injection needle puncture wounds via clot formation. Reduced bleeding from such wounds translates into a reduction in the number of healthcare worker exposures to a variety of blood-borne pathogens such as Hepatitis A, B, C, E, HIV, Meningitis, etc., during and after the administration of hypodermic injections, thereby reducing the inadvertent, yet inevitable transferring of such pathogens from healthcare workers to the general population. Reduced bleeding from such wounds further translates into reductions in the gross volume of biohazardous medical waste materials which are generated by healthcare workers during their attempts to control such bleeding. This further reduces the disease exposure hazards associated with the administration of hypodermic injections and reduces such exposure hazards for persons who handle or may accidentally come into physical contact with such biohazardous waste materials.

The present invention addresses and resolves specific medical inadequacies related to the hypodermic injection of vaccines and other injectable medicines, by providing a viable means for confirming the continuity-of-sanitization of patients' hypodermic injection sites, and for significantly improving the visibility of post-injection needle puncture entry wounds.

When the skin sanitizing/sterilizing solutions of the prior art are utilized to prepare hypodermic injection sites, it is often very difficult, if not impossible, for those who administer such injections to visually re-locate such treated skin areas, or to confirm that the treated skin areas receiving such injections have been properly and uniformly sanitized/sterilized, with any degree of certainty. Also, after having administered injections through such dubiously-prepared skin injection sites, it is often very difficult, if not impossible, for the administrators of such injections to visually relocate the post-injection needle puncture entry wounds, and this interferes with the proper bandaging of such wounds, which, in turn increases patients' risk of acquiring local and/or systemic infections via the inadvertent external contamination of such wounds. In addition, such post injection wounds frequently exhibit a lack of visibly-detectable bleeding or oozing, and frequently blend in with and become obscured by and indistinguishable from the various blemishes and naturally-occurring variations in skin surface pigmentation (such as freckles) which are often present within such skin injection site areas, thereby further complicating administrators' ability to precisely locate such wounds.

Consequently, the skin sanitizing/sterilizing solutions comprising the prior art are inadequate in their performance and reliability with regard to their ability to protect patients from becoming inadvertently innoculated with infectious microorganisms and microscopic parasites, and, with regard to their ability to help control bleeding from needle puncture wounds subsequent to patients' receiving hypodermic injections. The present invention resolves these inadequacies, thereby significantly decreasing such patients' risk of acquiring such infections consequent to receiving hypodermic injections.

The foregoing is particularly significant in its impact on public health, when one considers the massive number of injections, including immunizations, numbering in the many millions, which are given annually on a global scale in a multitude of settings and at an ever-increasing annual rate. On such a massive scale, any reduction in rates of infection ultimately translates into the saving of innumerable lives, as well as into large scale cost-savings in relation to the care and treatment of patients who acquire infections via this route. The present invention makes the administration of injectable medicines dramatically safer than it has been in the past, and has the potential to save innumerable lives and to reduce needless pain and suffering.

The Manufacture of the System of the Present Invention
Injection Site Visibility Enhancers As noted above, injection site visibility enhancers serve to demarcate both the injection sites themselves and the post-injection needle puncture entry wounds occurring therein, thus, facilitating proper post injection cleansing and bandaging of such wounds. Said injection site visibility enhancers useful in the practice of the present invention are suitable for use on human skin.

Injection site visibility enhancers useful in the practice of the present invention include, but are not limited to, polysaccharides such as chitosan and starch, TiO2, FDA approved food colorings, talc, Anthrapyrimidine Yellow (PY 108), Isoindolone Yellow R (PY110), Yellow Ochre PY ASTM, Anthrapyrimidine Yellow (PY 108), Isoindolone Yellow R (PY 110) ASTM 1, Pthalo Blue PB 15 & 16 ASTM 1, and Pthalo Green PG 7 ASTM 1, Green Earth PG 23 ASTM 1, Pyrrole Red PR 254 ASTM 1, Alizarin Crimson PR 83 ASTM 111, Quinacridone Red Y (PR 192), Napthol Red PR 17 ASTM 111, triarylmethane dyes, indigo dyes, xanthine dyes, quinophthalone, anthraquinone dyes, quinoline yellow (E104), patent blue V (E131), brilliant green BS (E142), various water color pigments (such as the Yellow Ochre PY ASTM 1), fluorescein, and carbocyanine dyes and mixtures thereof.

In the manufacture of the present invention, it should be noted that the weight to volume relationships of the various ingredients of the various embodiments of the present invention can be individually calculated using the following rudimentary equation, and that these relationships may vary from one embodiment to the next:

% weight/volume=weight in grams of the substance/
100 milliliters total volume of the liquid.

For example if 5 grams of a solid substance is dissolved or suspended in a total volume of 100 milliliters of a liquid, then the resulting fluid is a 5% solution or suspension of that solid substance. If 0.2 gm of a solid substance is dissolved or suspended in 100 milliliters total volume of a liquid, then the resulting fluid is a 0.2% solution or suspension of the solid substance.

Non-limiting examples of the ranges of the % w/v ratios for the various ingredients comprising the present invention include the following:
TiO2=1 gm-70 gm=1% w/v-70% w/v
Chitosan=20 gm-70 gm=20% w/v-70% w/v
Methylcellulose=1 gm-20 gm=1% w/v-20% w/v
DSS=0.01 gm-10 gm=0.01% w/v-10% w/v
Dehydrated Chitosan Carboxyalkylamide=20 gm-70 gm=20% w/v-70% w/v
Anthrapyrimidine Yellow (PY 108)=0.01 gm-10 gm=0.01% w/v-10% w/v
Chlorhexidine Gluconate Solution=1%-5% % wt/volume
Lidocaine Powder=0.5 gm-10 gm=0.5% w/v-10% w/v
Arylide Yellow G=0.1 gm-5 gm=0.1% w/v-5% w/v
Arylide Yellow 10G=0.1 gm-5 gm=0.1% w/v-5% w/v
Yellow Ochre=0.1 gm-10 gm=0.1% w/v-10% w/v
Polyvinylpyrrolidone (PVP K-30)=0.5 gm-20 gm=0.5%-20% w/v In an embodiment of the present invention chitosan is a suitable visibility enhancer.

In a further embodiment of the present invention TiO2 is a suitable visibility enhancer.

In another embodiment of the present invention chitosan and TiO2 are suitable visibility enhancers.

Injection Site Sanitizers

Injection Site Sanitizers useful in the practice of the present invention include, but are not limited to, isopropyl alcohol, benzalkonium chloride, ethyl alcohol, chlorhexidine Gluconate, Sodium Hypochlorite, commercially available hand sanitizers; and mixtures thereof.

Injection Site Coagulants

The present invention may optionally contain coagulants. The visibility enhancers, TiO2 and chitosan, also have coagulant properties. Physiologically-induced blood clotting at the said needle puncture wound entrance is enhanced by one or more blood coagulant ingredients present in the said deposited layer or coating. As the said layer or coating adjacent to the said wound entrance becomes progressively exposed to the said oozing blood/body fluids, its blood coagulant ingredient also becomes progressively exposed to the said oozing blood/body fluids, thereby initiating blood clot formation at the said needle puncture wound entrance. The coloration and physical appearance of the blood clot thus formed, demarcates the said needle puncture wound entrance in and of itself, and its visible presence simultaneously contributes to the visibility and location of the said wound entrance as stated in the previously-cited means.

Additional optional injection site coagulants useful in the practice of the present invention include, but are not limited to, microparticulate calcium carbonate, microparticulate corn starch, and microparticulate talc.

Injection Site Anesthetics

The system of the present invention may optionally contain topical anesthetics to alleviate discomfort at the injection site.

Injection site anesthetics useful in the practice of the present invention include, but are not limited to, Pramoxine, Lidocaine, Dibucaine, Prilocaine, Benzocaine, Tetracaine, and Ethyl Chloride Spray and mixtures thereof.

The following formulations represent non-limiting embodiments of the present invention:
Ingredients Comprising a Non-Limiting Example of the Present Embodiment as a Suspension:
Titanium Dioxide=50 grams per 100 milliliters total volume Chitosan=50 grams per 100 milliliters total volume
Methylcellulose (as suspending agent)=5 grams per 100 milliliters total volume
DSS (as surfactant/wetting agent)=0.1 grams per 100 milliliters total volume
Isopropanol or Ethanol (70%)=15 milliliters per 100 milliliters total volume.
Primary Vehicle qs.ad.=quantity sufficient to yield a total volume of 100 milliliters of final product.
Instructions for Formulating a Non-Limiting Example of the Present Embodiment as a Suspension:

The Primary Vehicle which is utilized in formulating the following example of a suspension, is, in this case, comprised of an aqueous/alcohol solution of 3% w/v of Chlorhexidine Gluconate, in which is dispersed, 5 grams of Methylcellulose.

The Secondary Vehicle which is utilized in formulating the following example of a suspension, is, in this case, comprised of 5 milliliters of Isopropyl or Ethyl Alcohol, in which is dissolved 50 milligrams of DSS.

The Primary Vehicle is formulated by dissolving 5 grams of Methylcellulose in approximately 10 milliliters of Isopropyl or Ethyl Alcohol, and incrementally adding this mixture, with rapid stirring, to a thermally cooled aqueous solution of 3% w/v of Chlorhexidine Gluconate, until a total volume of 100 milliliters is achieved, resulting in the uniform dispersion of the said Methylcellulose in the said Chlorhexidine Gluconate solution. The cooling of the said Chlorhexidine Gluconate solution prior to the addition of the said Alcohol/Methylcellulose solution, facilitates the dispersion of the Methylcellulose in the said Chlorhexidine Gluconate solution. The Chlorhexidine Gluconate solution should be cautiously stirred, and/or stirred within a gasless environment while adding the said Alcohol/Methylcellulose solution, in order to prevent the trapping of gas bubbles in the Primary Vehicle during its manufacture.

Equal parts (50 grams each) of the dry, particulate TiO2 and Chitosan ingredients are blended and the mixture is mechanically ground. In the first stage of the grinding process, the said dry mixture is thoroughly ground until the sizes of its particles fall within the range of >100 but <2000 .mu.m. Particles whose dimensions fall within this size range do not exhibit tactile grittiness, and consequently, when these particles are deposited in the form of a post-evaporation layer onto skin surfaces at hypodermic injection sites, this attribute is clearly advantageous.

In the second stage of the grinding process, the grinding of the dry, uniformly-particulate TiO2/Chitosan mixture is continued during the gradual, incremental introduction of 5 milliliters of the Secondary Vehicle into the grinding process, thereby effecting the thorough wetting or moistening of the said uniformly ground mixture by reducing the surface tension of its component ingredients.

The said ground and moistened mixture then exits from the second stage of the grinding process and is blended and mechanically mixed with the Primary Vehicle in a gasless environment such as an air-tight vessel. The Primary Vehicle is added to the said mixture in 2 milliliter increments during this mixing process, to facilitate the uniform suspension of the non-volatile ingredients in the Primary Vehicle. This incremental mixing process continues until it yields a total volume of 100 milliliters of suspension. To complete this mixing process, the said suspension is accumulated in a vessel which is devoid of air or other gasses. The said vessel is then mechanically agitated or its contents are sonicly agitated, thereby yielding 100 milliliters of finished product, which is highly opaque and has a lotion-like consistency.

Figure 4:
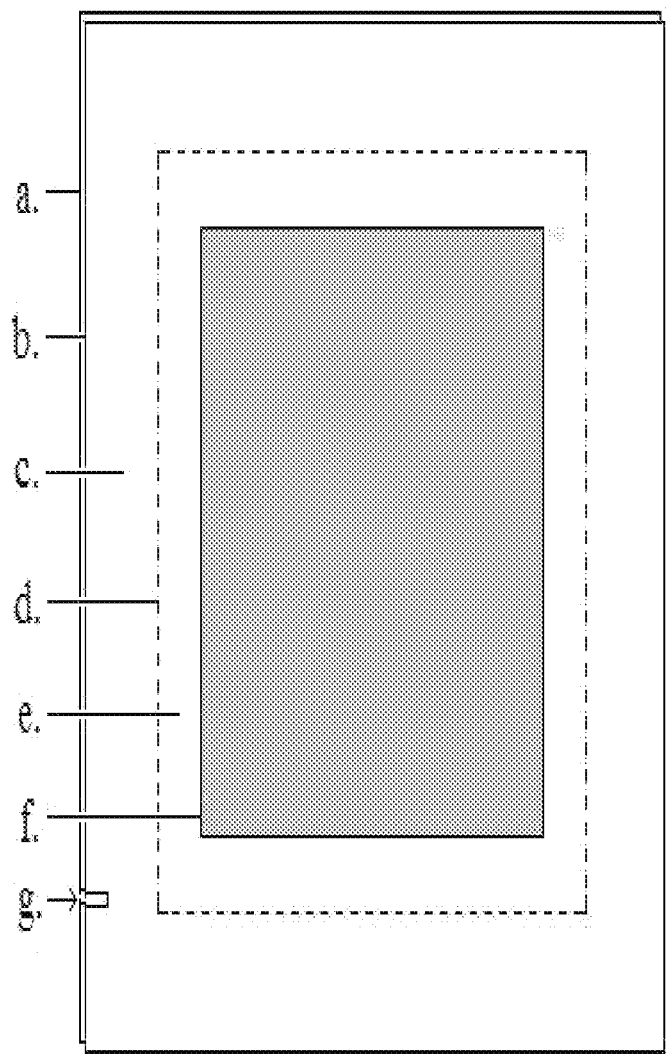
FIG. 4 illustrates the assembled and sealed components comprising FIGS. 2 and 3.

Approximately 1 to 1.5 milliliters of this suspension is injected into the packet comprising FIG. 4, just prior to its being sealed, thereby forcing out any residual air pockets from the interior of the said packet prior to the application of a sealing process to the said packet as cited herein. The packet comprising FIG. 4., is then sealed and the swab and suspension it contains are then ready for use in the field.
Ingredients Comprising a Non-Limiting Example of the Present Embodiment as a Slurry:
Titanium Dioxide=50 grams per 50 milliliters total volume
Chitosan=50 grams per 50 milliliters total volume
Methylcellulose (as a stabilizer)=2 grams per 50 milliliters total volume
DSS (as surfactant/wetting agent)=0.050 grams per 50 milliliters total volume
Isopropanol or Ethanol (70%) (as skin sanitizer)=5 milliliters per 50 milliliters total volume.
Primary Vehicle qs.ad.=quantity sufficient to yield a total volume of 50 milliliters of final product.
Instructions for Formulating a Non-Limiting Example of the Present Embodiment as a Slurry:

The Primary Vehicle which is utilized in formulating the following example of a slurry, is, in this case, comprised of a ⅓rd dilution of an aqueous solution of stabilized 3% sodium hypochlorite with 0.01% sodium hydroxide.

The Secondary Vehicle which is utilized in formulating the following example of a slurry, is, in this case, comprised of 5 milliliters of Isopropyl or Ethyl Alcohol, in which is dissolved, 50 milligrams of DSS.

A mixture comprising 50 grams each, of dry, particulate TiO2 and Chitosan, and 2 grams of dry methylcellulose is blended and mechanically ground. In the first stage of the grinding process, the said dry mixture is thoroughly ground until the particle size of each of its ingredients falls within the range of >100 but <2000 .mu.m. and it is uniform in its consistency, thereby preventing the occurrence of grittiness in the said post-evaporation deposited layer (comprised of the said non-volatile component ingredients), following the application of the said suspension to hypodermic injection sites.

In the second stage of the grinding process, the grinding of the dry, uniformly-particulate TiO2/Chitosan/Methylcellulose mixture continues, while the Secondary Vehicle is gradually and incrementally introduced into the grinding process, until a total of 5 milliliters of the secondary vehicle has been introduced, thereby effecting the thorough wetting of the said ground ingredients and reducing the mixture's surface tension.

The said ground and moistened ingredients then exit from the second stage of the grinding process and are co-mingled and mechanically mixed with the Primary Vehicle, which is added in 2 milliliter increments until a total volume of 50 milliliters of slurry is produced. To complete the mixing process, the said slurry is collected in a vessel which is devoid of air and which is mechanically agitated, or the slurry itself is sonicly agitated, thereby yielding a total and final volume of 50 milliliters of final product, which is opaque and has a creamy consistency. Approximately 1 to 1.5 milliliters of this slurry is injected into the packet comprising FIG. 4, just prior to its being sealed. The packet comprising FIG. 4., is then sealed and the swab and slurry it contains are ready for use when the packet is torn open.
Ingredients Comprising a Non-Limiting Example of the Present Embodiment as a Gel:
Dehydrated Chitosan Carboxyalkylamide Hydrogel=50 grams
Anthrapyrimidine Yellow (PY 108)=0.2 gram Primary Vehicle qs.ad.=quantity sufficient to yield a total volume of 100 milliliters of final product.

Instructions for Formulating a Non-Limiting Example of the Present Embodiment as a Gel:

The Primary Vehicle which is utilized in formulating the following example of a Gel, is, in this case, comprised of a commercially available Hand Sanitizing Gel, having, for example, 62% Ethyl Alcohol as its primary sanitizing agent. Commercially-available Hand Sanitizing Gels, such as those containing one or more alcohols, are well known in the art and are acceptable for use in the present invention.

The Secondary Vehicle which is utilized in formulating the following example of a Gel, is, in this case, comprised of 0.1 gram of DSS and 0.2 gram of Anthrapyrimidine Yellow (PY 108) which are dissolved in 10 milliliters of the Primary Vehicle.

The Secondary Vehicle is blended into the said 50 grams of Dehydrated Chitosan Carboxyalkylamide Hydrogel in 2 milliliter increments, thereby thoroughly wetting and colorizing it. This blended mixture, comprising the moistened, colorized and surfactant-treated Dehydrated Chitosan Carboxyalkylamide Hydrogel is then further blended with the Primary Vehicle in graduated increments until total volume of 100 milliliters is attained. Approximately 1 to 1.5 milliliters of this Gel is injected into the packet comprising FIG. 4, just prior to its being sealed. The packet comprising FIG. 4., is then sealed and the swab and Gel it contains are ready for use when the packet is torn open.

Ingredients Comprising Another Non-Limiting Example of the Present Embodiment as a Gel:
Chitosan Carboxyalkylamide Hydrogel=100 milliliters total volume
3% w/v of Chlorhexidine Gluconate=3 milliliters
Anthrapyrimidine Yellow (PY 108)=0.2 gram
Lidocaine Powder (topical anesthetic)=0.5 gram Instructions for Formulating Another Non-Limiting Example of the Present Embodiment as a Gel:

The Primary Vehicle which is utilized in formulating the following example of a Gel, is, in this case, comprised of the Chitosan Carboxyalkylamide Hydrogel, which is formulated according to Laugier, et al., as disclosed in U.S. Pat. No. 8,236,781, and referenced herein.

The Secondary Vehicle which is utilized in formulating the following example of a Gel, is, in this case, comprised of 3 milliliters of Chlorhexidine Gluconate, 0.5 gram of Lidocaine, and 0.2 gram of Anthrapyrimidine Yellow (PY 108) which are dissolved in 20 milliliters of the Primary Vehicle.

The Secondary Vehicle is then blended with the Primary Vehicle until a total volume of 100 milliliters of final product is attained. Approximately 1 to 1.5 milliliters of this Gel is injected into the packet comprising FIG. 4, just prior to its being sealed. The packet comprising FIG. 4., is then sealed and the swab and Gel it contains are ready for use when the packet is torn open.

Ingredients Comprising a Non-Limiting Example of the Present Embodiment as a Solution:
FD&C Blue 1 (as visibility enhancer)=6 milliliters per 100 milliliters total volume
DSS (as topical surfactant)=0.1 gram per 100 milliliters total volume
Primary Vehicle qs.ad.=quantity sufficient to yield a total volume of 100 milliliters of final product.

Instructions for Formulating a Non-Limiting Example of the Present Embodiment as a Solution:

The Primary Vehicle which is utilized in formulating the following example of a solution, is, in this case, comprised of 91% Isopropyl Alcohol, in which is dissolved 6 milliliters of the Food Coloring FD&C Blue 1, and 0.1 gram of DSS, to yield a total of 100 milliliters of final product. Approximately 1 to 1.5 milliliters of this Solution is injected into the packet comprising FIG. 4, just prior to its being sealed. The packet comprising FIG. 4., is then sealed and the swab and Solution it contains are ready for use when the packet is torn open. The application of the said mixture to a hypodermic injection site via the said patch will effect the formation of a post-evaporation deposited layer having faint blue coloration which is sufficient to demarcate the said injection site and to occlude the skin blemishes residing beneath it. This solution does not have coagulative properties, but is still efficacious for use in hypodermic injection site sanitization and demarcation, and it can also be utilized as a Primary Vehicle in one or more of the other embodiments of the present invention.

Ingredient Combinations Comprising Non-Limiting Examples of the Present Embodiment as Aerosols:
Arylide Yellow G=0.5 gram per 100 milliliters total volume
Arylide Yellow 10G=0.5 gram per 100 milliliters total volume
Yellow Ochre=1 gram per 100 milliliters total volume
   OR
Arylide Yellow G=0.5 gram per 100 milliliters total volume
Arylide Yellow 10G=0.5 gram per 100 milliliters total volume
Yellow Ochre=1 gram per 100 milliliters total volume
Chitosan Carboxyalkylamide=1 gram per 100 milliliters total volume
   OR
Arylide Yellow G=0.5 gram per 100 milliliters total volume
Arylide Yellow 10G=0.5 gram per 100 milliliters total volume
Yellow Ochre=1 gram per 100 milliliters total volume
Titanium Dioxide=1 gram per 100 milliliters total volume
   OR
Yellow Ochre=2 grams per 100 milliliters total volume
   AND
DSS (as surfactant/wetting agent)=0.1 gram per 100 milliliters total volume
Polyvinylpyrrolidone (PVP K-30) (as stabilizer)=1 gram per 100 milliliters total volume.
Ethyl Chloride qs.ad.=quantity sufficient to yield a total volume of 100 milliliters of final product.

Instructions for Formulating One or More Non-Limiting Examples of the Sixth Embodiment as a Combined Solution/Suspension for Use as Aerosols:

In this first, non-limiting example of such formulations: dissolve 0.5 gram of Arylide Yellow G and 0.5 gram of Arlide Yellow 10G in approximately 50 milliliters of Ethyl Chloride. Physically combine 1 gram of the non-volatile, micro-particulate ingredient Yellow Ochre, with 0.1 gram of DSS and 1 gram of powdered PVP K-30. Mechanically grind these ingredients together until thoroughly mixed, and then gradually blend the resultant ground mixture into the 50 milliliters of the Arylide Yellow/Ethyl Chloride solution. Gradually add additional Ethyl Chloride to the said blended mixture, to a total volume of 100 millimeters. The final product is then packaged in a pressurized, organic solvent-resistant container, which is then sealed with an organic solvent-resistant, clogging-resistant dose metering valve which is configured to dispense 1 to 2 milliliters of product per each downward actuation of the said metering valve's actuator, "f." of FIGS. 5. *a*. and *b*. The said actuator should be positioned approximately 7.5 centimeters from the injection site target area, prior to actuation.

The other ingredient combinations cited above are formulated in a similar manner, using the measured quantities listed for each of the cited ingredients in each variation, and formulating them according to the instructions disclosed above, in the "first, non-limiting example of such formulations"

The non-volatile ingredient combinations of the other listed variations cited above are measured, combined, and processed in the same or similar manner, thereby formulating each of the other product variations cited above. The application of any of the said variant mixtures to a hypodermic injection site, via spraying, will effect the formation of a post-evaporation deposited layer having highly visible yellow coloration, which is sufficient to demarcate the said injection site, "c.", and to occlude or reduce the visibility of the skin blemishes residing beneath it.

Common food coloring dyes, such as FD&C Blue 1, alone or in various combinations with other such dyes, can be formulated using alcohol and/or aqueous based vehicles, to which at least one skin sanitizer, such as Chlorhexidine or Sodium Hypochlorite has been added. The ingredient quantities and preparation of these formulations will follow those disclosed in the previous embodiments of the present invention; the only difference being that they will be packaged and utilized as disclosed in the present embodiment.

The present invention relates to compositions and methods of preparing said compositions for topically-applied, pigment/tint/dye/colorant-enhanced, body-fluid-reactive, blood coagulant-enhanced, skin injection site sanitizing/sterilizing solutions/suspensions/slurries, each of which, when physically applied to human skin prior to the hypodermic injection of medicines such as vaccines, antibiotics, insulin, etc., via subcutaneous, intramuscular, and intravenous routes, significantly protects and improves patients' health in a number of very distinct and unique ways, in relation to their receipt of such injections. Each of the said formulated variations thereof, is comprised of a "volatile component" having at least one fluid ingredient, which may act as a solvent and/or suspending vehicle, and a multi-ingredient "non-volatile component" which is dissolved and/or suspended in, and/or milled into a slurry with the said "volatile component".

One or more of the ingredient(s) comprising the said "volatile component" are selected based on: the broadness of their spectrum of antimicrobial activity; the speed at which they evaporate from human skin surfaces to which they are topically applied; and, their safety for human use when topically applied; thereby optimizing their performance within the context of the present invention. The optimized formulation of the said "volatile component" is derived through use of empirical experimentation as cited by example elsewhere herein, utilizing means and methods which are well known and established in the art, in order to achieve optimal levels of performance for each of the said components as well as for each of the individual ingredients of which the said components are comprised. The said "volatile component" is selected for its ability to: sanitize and ideally sterilize human skin surfaces to which it is applied; evaporate rapidly from such skin surfaces; and, to act as both a solvent for the soluble fraction of the said "non-volatile component" and/or as a fluid vehicle for the less-than-soluble or insoluble fraction of the said "non-volatile component". The said "volatile component" is comprised of one or more solvents, such as isopropyl alcohol, which is utilized, alone or in combination with other such solvents and/or fluids, both as a skin sanitizing/sterilizing agent, and as a fluid vehicle for transporting and applying the said dissolved and/or suspended "non-volatile component" to a pre-selected hypodermic injection site, all such solvents and/or fluids preferably having functionally-identical or functionally-similar physical, antimicrobial and evaporative properties.

The said multi-ingredient "non-volatile component" is comprised of a mixture of physically and/or chemically-compatible sub-component ingredients which include but are not limited to chemical substances which are selected from one or more relevant chemical categories such as the following: surfactants; fluorescent and/or non-fluorescent pigments, dyes, colorants or tints; blood coagulants; and, suspending agents, if required for proper admixture. The selection of each chemical substance from each of the said categories is based on the degree of relevancy of its properties and characteristics in relation to its applied use within the context of the present invention. The properties and characteristics of such categorized chemical substances are well known and are amply described in the literature of relevant prior art. A non-limiting example of a chemical substance which is to be selected from such a relevant category is dioctyl sodium sulfosuccinate or "DSS", which is selected from the said "surfactant" category. "DSS" meets the functional criteria for inclusion in the said "non-volatile component" of the present invention, because of its physical properties which include its ability to lower the surface tension of fluids. This ability is utilized in the present invention to lower the surface tension which may exist between the topically applied solution/suspension/slurry comprising the present invention and the skin at the hypodermic injection site to which it is applied, thereby resulting in the deposition of a more uniform, post-evaporation layer comprising the ingredients of the said "non-volatile component". The ability of DSS to reduce surface tension has also led to its widespread medical use as a stool softener, which attests to its safety. It is acknowledged that other chemical substances having functionally similar surface tension-reducing properties may be utilized in the present context, and that their use is to be included within the scope and intent of the present invention. Thus, each of the said relevant chemical categories is comprised of one or more chemical substances such as those cited herein, which are adaptable for use in, and desirable for inclusion in a particular "non-volatile component" mixture comprising one or more of the preferred embodiments of the present invention, and their use in this context is also to be included within the scope and intent of the present invention. Several of the numerous, possible formula variations of the said multi-ingredient, non-fluid, "non-volatile component" are disclosed, and at least one of these is combined with at least one of the variations comprising the said "volatile component", resulting in a variety of possible formulations of the "solution/suspension/slurry" comprising the present invention.

When the said "volatile component" and the said "non-volatile component" ingredients are mixed in accordance with an empirically-derived and optimized formula, and are applied to a human skin injection site, e.g.: at the deltoid muscle, the said "volatile component" sanitizes or ideally sterilizes the said injection site and quickly evaporates therefrom, leaving behind a thinly deposited layer or coating comprised of a mixture of the ingredients comprising the said "non-volatile component".

The Merriam Webster Online Dictionary's medical definition of the term "slurry" is: "a watery mixture of insoluble matter". In terms of physical chemistry, the ingredients in a slurry are not necessarily totally insoluble or non-suspendable in the fluids in which they are mixed, and water is not necessarily the fluid-of-choice for compounding such a mixture. Most substances exhibit some inherent degree of solubility or suspendability in the fluids in which they are mixed, even if deemed "insoluble" or "not suspendable" according to their descriptive literature, and this is the context in which the term "slurry" is utilized in the present invention. It is noted that the definition of this term is herein broadened from its original version, and is herein defined as being comprised of a microscopically-ground, grit-free mixture of the ingredients comprising the said "non-volatile component" which is moistened with a sufficient volume of the said "volatile component" via mechanical or other means, thereby formulating a fluid slurry comprised of the said mixture of the said "volatile component" and the said "non-volatile component".

With regard to the present invention, these mixtures may be comprised of a conglomeration of a partial solution, a partial suspension and/or a partial slurry of the individual ingredients comprising the said "non-volatile component", each ingredient of which may be partially dissolved by and/or partially suspended in, and/or partially slurried by, the said "volatile component". The formulation of such mixtures is plausible because each of the individual ingredients may be at least partially soluble and/or partially suspendable in the said "volatile component". Each such ingredient may also have an insoluble fraction which may have to be physically suspended in the said "volatile component" via the use of one or more suspending agents and/or surfactants. Furthermore, some ingredients may have fractions which prove to be neither soluble nor suspendable, and these remaining fractions of such ingredients are moistened with a measured volume of the said "volatile component" of sufficient quantity to form a partial slurry thereof, achieved by utilizing one or more known mechanical processes such as the fine grinding of the said components in the presence of one or more surfactants if required. The resultant conglomerate mixtures comprising one or more embodiments of the present invention have elements of, and are comprised of a combination of these 3 physical states.

Each of the said formula variations of the said "solution/suspension/slurry" comprising the present invention, when applied to human skin, is formulated to:

visually demarcate the areas of, and the boundaries of the injection site skin surfaces to which it is applied;

visually occlude or mask any underlying skin blemishes, such as freckles, residing beneath such demarcated skin surfaces;

enable the administrators of injectable medicines to determine the continuity-of-sanitization of such demarcated skin surfaces by enabling them to visually examine and evaluate the uniformity of the coloration of such demarcated skin surfaces with regard to the absence or presence of gaps in such coloration, and to utilize the absence or presence of such gaps as indicators which determine whether or not such demarcated skin surfaces have been uniformly sanitized consequent to the topical application of the solution/suspension/slurry of the present invention to such skin surfaces;

physically and/or chemically react with body fluids oozing from post-injection needle puncture wounds occurring within the demarcated areas of such treated skin surfaces, thereby dramatically improving the visibility and accuracy of the bandaging of such wounds;

possibly contribute to the sanitization of such demarcated skin areas, dependent upon the properties of the pigment(s), colorant(s) or tint(s) selected for use; and, initiate clot formation at such post-injection needle puncture wounds, thereby reducing bleeding from such wounds and further increasing the visibility of, and the accurate bandaging of such post-injection needle puncture wounds.

The concentrations of the individual ingredients comprising the said "non-volatile component" of the "solution/suspension/slurry" comprising the present invention, must be sufficient to ensure the deposition of a uniform, post-evaporation layer or coating comprised of such ingredients, which is of adequate density and coloration to enable it to functionally perform as disclosed herein. The said deposited layer or coating accurately demarcates the treated skin injection site and facilitates the administration of injectable medicines at such sites, by providing the administrators of hypodermic injections with a uniformly sanitized and colorized, visually-identifiable target area, within which such medicines are injected. When an injection is administered within the said target area, and the hypodermic needle is withdrawn from the skin, the location of the post-injection needle puncture entry wound becomes obviously visible to the administrator of the said injection, due to interactions between the ingredients comprising the deposited layer and the blood/body fluids oozing from the said needle puncture entry wound, thereby facilitating more accurate placement of a bandage to cover the said wound. This is especially beneficial in patients who do not bleed detectably following the administration of such injections, which is a frequently-occurring phenomenon. In such patients, if conventional means, such as those disclosed in the prior art, are utilized to prepare their skin injection sites, their post-injection needle puncture entry wounds are often visually obscured by the presence of proximate skin blemishes, such as freckles, making the visual identification and location of such wounds difficult if not impossible, thereby interfering with the proper bandaging of such wounds, which increases patients' risk of infection at such wound sites.

EMBODIMENTS OF THE PRESENT INVENTION

In this first non-limiting example of a preferred embodiment of the present invention, titanium dioxide—$TiO2$ (also known as titania, titanium white, Pigment White 6, CI 77891, or, as the food coloring E171) is incorporated into the "non-volatile component" of the present invention as a visually-occlusive, skin pigmenting/tinting agent. This $TiO2$-enriched "non-volatile component" is then mixed with the above-cited "volatile component" to produce the solution/suspension/slurry comprising this embodiment of the present invention. $TiO2$ is intensely white in coloration and in its dried state is capable of fluid adsorption. This effect is enhanced via the addition of at least one surfactant, such as DSS, to at least one of the above-cited components. When the solution/suspension/slurry comprising the present embodiment is applied onto an untreated area of human skin, "a.", FIG. 1, at skin injection site area "c.", the said "volatile component" evaporates from the said skin surface, resulting in the formation of a thin, uniformly deposited layer comprised of $TiO2$ which, if properly applied, uniformly coats all of area "c.". Border "b." differentiates the untreated area of skin, "a." from the said treated and coated area of skin, "c." The deposited layer thus formed over skin area "c.", FIG. 1, exhibits uniform and intensely white coloration, which opacifies the underlying skin over which it has been deposited.

One non-limiting example, of a number of possible reactions which can occur between the said body fluids which ooze from the said needle puncture wound at the skin surface wound opening, "e.", FIG. 1., and the said thinly deposited layer of opacifying, pigmenting/tinting agent(s), at "c.", is comprised of, in the present case, a physical reaction which occurs between the said oozing body fluids and the said deposited layer comprised of TiO2, which has been treated to improve its ability to maintain a uniform dispersion in a "volatile component", via means cited in the prior art. The normal coloration of the said deposited layer of TiO2 is intensely white, and the minute quantities of the said body fluids oozing from the said needle puncture entry wound, "d." at wound opening, "e.", are sufficient to produce a visually discernible, physical discoloration of the said deposited layer of TiO2 in the form of a small, progressively expanding ring-shaped area, "f.", FIG. 1., which encircles the roughly circular, skin surface wound opening, "e.", of the said needle puncture entry wound, "d.". In the event that the said oozing is insufficient to cause a visible discoloration at the said skin surface wound opening, "e.", the said needle puncture entry wound, "d.", would still have sufficient visual contrast in comparison to the surrounding, uniformly deposited layer of TiO2, to make the said needle puncture entry wound, "d.", easily visible to the administrator of such an injection.

The progressive lateral expansion of the said ring-shaped area "f.", of FIG. 1, proceeds as follows: A hypodermic injection is administered within the treated area "c." of FIG. 1, thereby forming the hypodermic needle puncture entry wound, "d." and its associated skin surface wound opening, "e.". The said skin surface wound opening, "e.", directly borders on and is in direct physical contact with the adjacent portion of the said deposited layer comprised of, in this case, TiO2. Following the withdrawal of the said needle from the skin, the said body fluids progressively ooze from the needle puncture entry wound, "d.", and come into direct physical contact with the adjacent portion of the said deposited layer of TiO2 at the skin surface wound opening, "e.". The said deposited layer of TiO2 adjacent to the said skin surface wound opening, "e.", progressively adsorbs the said progressively oozing body fluids, resulting in the formation of a progressively expanding, ring-shaped area, "f.", comprised of discolored TiO2 which visibly contrasts against the intensely white, opacified background of the un-discolored remainder of the said deposited layer of TiO2. This contrast in coloration between the discolored and un-discolored TiO2 areas, coupled with the said deposited layer's occluding or masking of underlying skin blemishes, is sufficient to enable the administrator of the said injection to visually acquire the precise location of the said skin surface wound opening, "e." of the said needle puncture entry wound, "d.", prior to bandaging it.

This preferred embodiment of the present invention also addresses the additional problems associated with excessive bleeding from such post-injection needle puncture entry wounds. Excessive, instantaneous bleeding often occurs from such wounds, following the withdrawal of the needle from the skin, notably following intramuscular injections. The present embodiment reduces such bleeding via the inclusion of one or more known topically-applied blood coagulants such as chitosan, in one or more of its usable forms or derivatives, including but not limited to: the dehydrated, powdered form of the hydrogel chitosan carboxyalkylamide; chitosan silver complex; nano-particulate chitosan; and/or collagen. It should be noted that some forms of powdered chitosan silver complex may be more suited for application to inanimate objects rather than human skin, because of possible presence of residual traces of acetic acid and acetonitrile. In more concentrated form, acetic acid and acetonitrile are irritating and toxic. If traces of such irritants cannot be fully removed, then an alternate powdered form of chitosan is substituted in the present embodiment, such as the dehydrated hydrogel comprised of chitosan carboxyalkylamide. The inclusion and use of such coagulants in the present invention is intended to effectively reduce the rate of bleeding from such wounds. This reduction in bleeding decreases healthcare worker exposure to blood-borne pathogens, which, in turn, decreases the proliferation of the diseases associated with acquiring such pathogens. In addition, external clot formation at such needle puncture entry wound openings increases the visibility of such wounds, which contributes to greater visibility and more accurate bandaging of such wounds. A detailed explanation of the inclusion and use of such blood coagulants in this first embodiment of the present invention is disclosed below.

Finely powdered titanium dioxide, a well known commercially available opacifier, is treated to improve its ability to maintain a uniform dispersion in the "volatile component" comprised of at least one solvent or reagent such as isopropyl alcohol. Numerous methods for such treatment of titanium dioxide exist and are well known in the art, especially in the field of physical chemistry as it relates to the production of various cosmetic skin products, including the so-called, commercially-available "Sun Blocking Lotions", which are used to protect human skin against ultraviolet solar radiation. Particle size of the TiO2 and any other non-volatile components should fall within the specific range required to avoid detectable, tactile grittiness when applied to a skin surface, eg. >100, but <2000 .mu.m. The said "volatile component" must also be selected for its ability to kill or attenuate most, if not all of the known pathogenic organisms on contact, when applied to human skin surfaces. In this embodiment of the present invention, the said "volatile component" is comprised of Isopropyl Alcohol in an overall concentration known to kill or disable such pathogens on contact (approximately 70 to 91%). Additional "non-volatile component" ingredients are added to this formulation, including, but not being limited to the following:

at least one commercially available, hypoallergenic, pharmaceutical and/or cosmetic grade suspending agent, such as one of those in the methylcellulose group of such compounds, which is utilized to uniformly suspend the said titanium dioxide in the isopropyl alcohol, in which it is otherwise poorly soluble, such suspending agents being well known in the art, and being found in common and prolific use in numerous commercial products;

at least one commercially available, hypoallergenic, cosmetic and/or pharmaceutical surfactant, such as "DSS", which is added to the said formulation in order to facilitate its suspension in the said "volatile component", to reduce the surface tension which may form at the boundary which separates the said topically applied formulation from the often oily human skin surfaces to which it is applied, thereby effecting the deposition of a more uniform post-evaporation layer at a formulation-treated skin injection site; and, at least one commercially available blood coagulant, such as chitosan or one or more of its usable forms or derivatives, including but not limited to: dehydrated chitosan carboxyalkylamide; chitosan silver complex; nano-particulate chitosan; collagen; and possibly thrombin (if its inherent stability issues can be resolved in the present context). One or more of such coagulants are added to the said formulation in a concentration sufficient to induce rapid surface and/or subsurface clotting at post-injection needle puncture entry wounds, thereby reducing excessive bleeding from such wounds while also contributing to their visibility and visual identification prior to bandaging. It should be noted that if thrombin is considered for use in the present context, its stability issues must be resolved, and a "volatile component" other than an alcohol should be considered, because of alcohol's ability to denature proteins such as thrombin. It should be noted that the "volatile component" of the present invention can be comprised of aqueous and/or non-aqueous solutions of one or more germicidal chemicals, or combinations of germicidal chemicals which may include chlorhexidine gluconate, sodium hypochlorite, etc, in concentrations which are sufficient to attenuate or preferably kill topically dwelling pathogens on contact.

Figure 2:
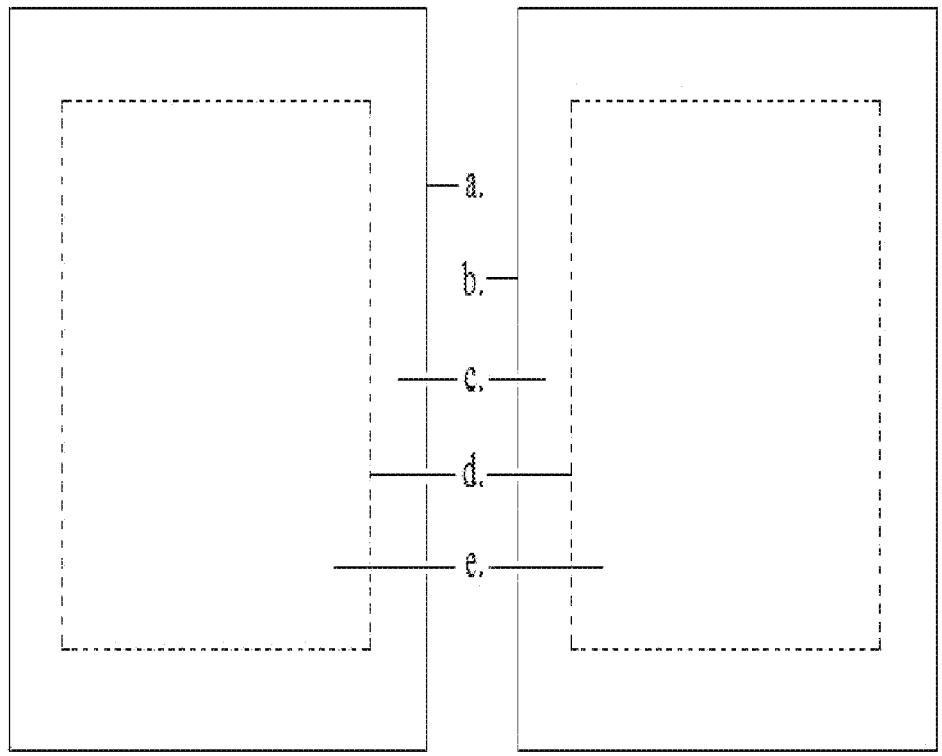
FIG. 2 illustrates an unassembled view of the individual components comprising one possible preferred embodiment of the present invention, including a disposable, adsorbent fabric or sponge-like patch, swab, or wipe, "f.", the surface of which will adsorb a quantity of at least one of the skin injection site sanitizing/sterilizing solutions/suspensions/slurries comprising the present invention.
Figure 2:
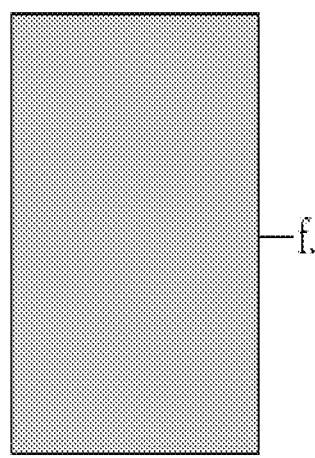
Figure 3:
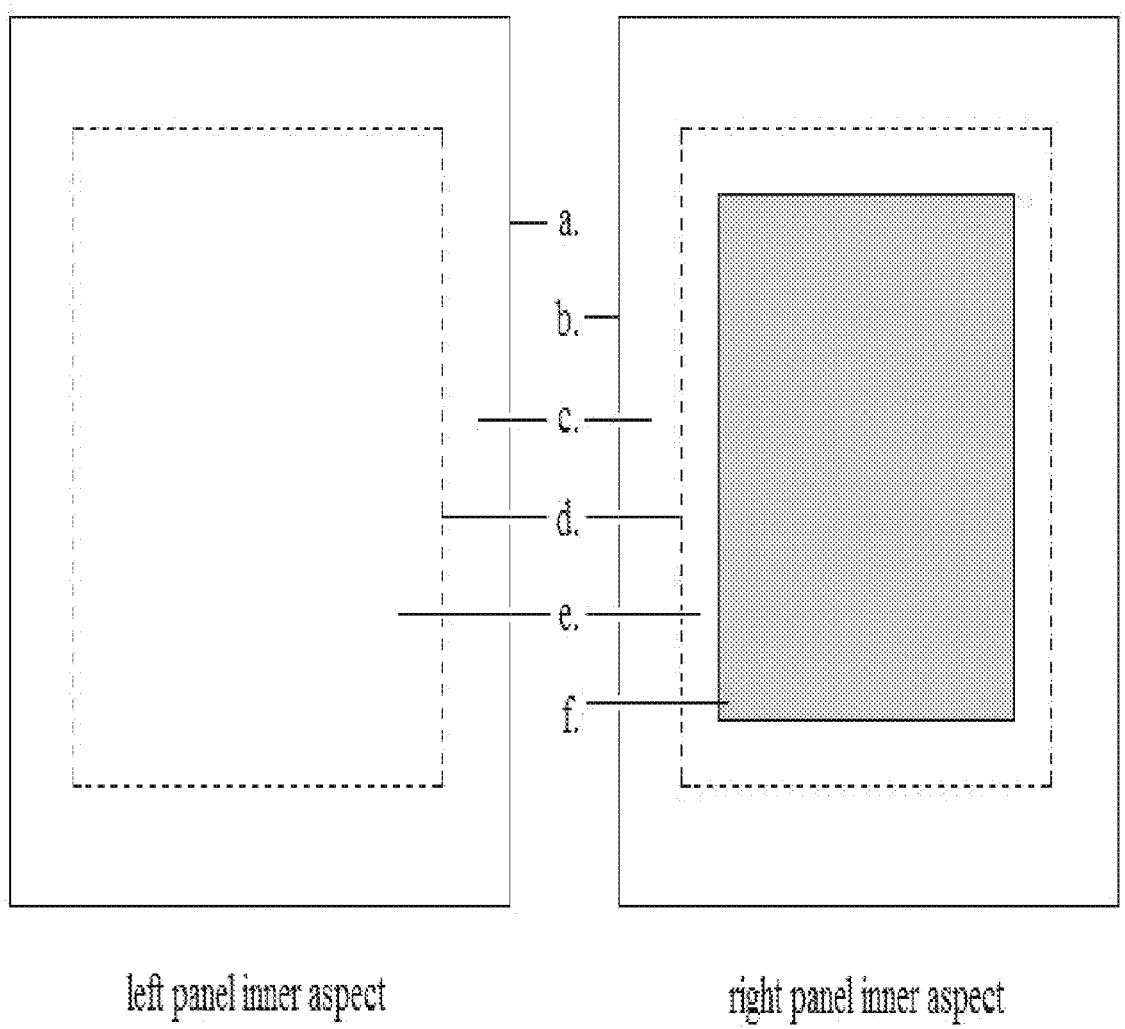
FIG. 3 illustrates the relational alignments of the components comprising FIG. 2, prior to their assembly and the application of a sealing process to areas "c" of both panels, thereby forming a sealed packet containing a patch, swab or wipe, "f.", the surface of which has adsorbed a quantity of at least one of the skin injection site sanitizing/sterilizing solutions/suspensions/slurries comprising the present invention.

Although the said "swabs" or "wipes" of the present invention are referred to herein as being comprised of "cloth" or "disposable fabric or sponge-like" materials; that such materials are described as absorbing rather than adsorbing one or more of the solutions/suspensions/slurries comprising the present invention; and that, in some examples, such materials are described as becoming saturated with one or more of such solutions/suspensions/slurries, it is understood and affirmed that, by preference, the said "swabs" or "wipes" of the present invention, which are illustrated as "f." in FIGS. 2 through 4, must themselves be made of one or more materials which are capable of adsorbing rather than absorbing most of the solutions/suspensions/slurries comprising the present invention. References herein, to the "saturation" of such swabs or wipes with one or more of such solutions/suspensions/slurries, are to be interpreted in the context of the present invention as primarily defining the phenomenon of adsorption rather than absorption in most cases.

Preferably, the said "swabs" or "wipes" disclosed in the present invention are comprised of materials which are non-porous and non-woven, in order to prevent them from wicking away the said "volatile component" of the present invention. Such wicking would leave the said "non-volatile component" in a semi-dry, un-appliable and unuseable state. The use of swabs or wipes which are comprised of such non-porous, non-woven materials ensures that these solutions/suspensions/slurries will remain intact when they are physically transferred from such swabs or wipes onto the skin surfaces at hypodermic injection sites. An example of such a non-porous, non-woven material is DuPont's Tyvek, which is composed of non-directional, high density polyethylene fibers which have first been spun and then bonded together by heat and pressure. The "swabs" or "wipes" of the present invention utilize a modified form of this material, the surfaces of which have been mechanically and/or chemically abraided to increase their surface area, thereby improving the treated material's ability to physically adsorb the solutions/suspensions/slurries comprising the present invention. Thus, this abraided material functions to physically adsorb the said solutions/suspensions/slurries onto its surfaces, without wicking away the said "volatile component" thereof, thereby leaving these solutions/suspensions/slurries physically intact and ready for topical application to such skin surfaces.

The present invention utilizes mechanical abraision as a means to increase the said "swab" material's surface area. Means and methods for mechanically-abraiding fabrics are well known in the prior art, and these are utilized in the present invention to abraid the external surface(s) of Tyvek or other functionally-similar materials, thereby rendering them useable as "swabs" for the topical application of the solutions/suspensions/slurries comprising the present invention. It should be noted that the surface tension present at such abraided surfaces may hinder the said swab's ability to physically adsorb of one or more of the said solutions/suspensions/slurries. This problem can be resolved by treating such abraided surfaces with at least one surfactant, such as DSS, thereby lowering their surface tension and facilitating the adsorption of the said solutions/suspensions/slurries onto the said materials' abraided surfaces. Tyvek's use as a base material is cited by reference herein, and its modification by abraision, for use in the present invention is herein disclosed and claimed, as is the use of similar materials in the present context.

The ability of such swab materials to adequately adsorb the solutions/suspensions/slurries comprising the present invention ensures that the said "swab" or "wipe" will physically transfer a volume of approximately 1 milliliter of any of these formulations, in a physically intact form, from the said "swab" or "wipe" onto the skin surfaces at hypodermic injection sites, thereby resulting in the deposition of post-evaporation barrier layers onto such skin surfaces. Such deposited layers then function as disclosed herein. In stark contrast to the foregoing, if the porous fabric-like material comprising the swabs or wipes of the prior art were to be substituted for use in the present invention, such wicking away of the said "volatile component" would immediately occur during the manufacture and containment of such "swabs" or "wipes" in their sealed packets, rendering the materials disclosed in the prior art unuseable in the present invention.

It is well understood in the prior art, that chitosan itself, is insoluble in aqueous solutions as well as in organic solvents. Titanium dioxide is also relatively insoluble as well, which necessitates the use of one or more surfactants and suspending agents in this and other embodiments of the present invention, if these or other insoluble or poorly soluble non-volatile ingredients are to be utilized. Although chitosan is soluble in dilute, aqueous organic acid solutions, such as solutions comprised of acetic acid, citric acid, etc., the use of chitosan dissolved in such solutions in association with the coating of hypodermic injection sites in the context of the present invention, is inadvisable, as it could cause pain and discomfort during and after the administration of such hypodermic injections. The present invention utilizes an inexpensive and safe method for circumventing such solubility issues by simply making a "slurry" of the said mixture of the "non-volatile component" ingredients, by mechanically wetting them and milling/grinding them with the said "volatile component", which is added in a quantity sufficient to allow the said "slurry" to have a consistency which will enable it to be smoothly, evenly, and thinly applied to a skin surface by means such as the disposable fabric or sponge-like patch, swab, or wipe disclosed in FIGS. 2.-4., and adding a surfactant as a wetting agent during the wetting and milling/grinding processes, if necessary to improve the said consistency of the said slurry. Ideally, with regard to the automated processes pertaining to the manufacturing of the sealed packet comprising FIG. 4.: the said disposable, fabric or sponge-like patch, swab, or wipe "f.", shown in FIGS. 2.-4., is physically saturated with a uniformly-consistent and accurately-measured quantity (e.g.: 1 to 1.5 ml) of the said solution/suspension/slurry comprising the present invention, during the process of assembly of the illustrated components, and the application of the said sealing process to the areas "c.", of the right and left panels, "a." and "b." of FIGS. 2.-4. Prior to the sealing of the packet illustrated in FIG. 4., the said accurately-measured quantity of the said solution/suspension/slurry is applied to and saturates the said patch, swab or wipe, "f.". This saturation should be performed immediately after, or shortly after the said solution/suspension/slurry exits from the said slurry milling process, and immediately before the packet-sealing process is applied to areas "c.", thereby producing sealed packets containing the said saturated patches, swabs or wipes, all of which are consistently identical in their qualitative and quantitative content. Manufacturing processes such as those which are well known in the art and which are in current commercial use, are readily adaptable by those skilled in the art, for use in manufacturing the disposable, fabric or sponge-like patch, swab, or wipe, "f.", comprising the present invention. The said consistency of the slurry and the proportion of its "volatile component" to its "non-volatile component" must be such that the said "volatile component" evaporates rapidly after the said slurry is applied to a skin surface, thereby effecting the rapid and uniform deposition of a thin, visually-occlusive, post-evaporation layer comprised of the said "non-volatile component", which covers the skin surface to which it was applied.

With regard to the overall formulation of this preferred embodiment of the present invention, the quantitative relationships of each of the individual sub-component ingredients of the said "non-volatile component", both to one another, and to the "volatile component" in which they are suspended and/or dissolved, are expressed in terms of W/V (weight-to-volume) and/or W/W (weight-to-weight) ratios. The isopropyl alcohol content of such a devised formula should also approach or exceed 70%, which has been the current standard for killing most topically-dwelling pathogens via the denaturing of their proteins, etc.

With regard to this first embodiment of the present invention, the selection of each of the individual sub-component ingredients comprising its "non-volatile component" is based on empirical studies which are precisely designed and conducted to:

identify those individual ingredients which will perform most optimally within the context of the present invention and which have properties which are the most relevant thereto;

determine the optimal concentrations of each of the said empirically selected, optimally-performing ingredients, in relation to each other, and/or in relation to the overall formulation of this embodiment as a whole;

determine the optimal quantity of each of the said empirically selected, optimally-performing sub-component ingredients, in relation to the density of the said deposited, post-evaporation layer comprised of the said sub-component ingredients of the "non-volatile component", in order to yield an optimally-performing post-evaporation deposited layer having sufficient density to perform as disclosed herein; and, include the said calculated optimal quantity of each of those optimally-performing sub-component ingredients into the formulation of the said optimized "non-volatile component", thereby enabling it to perform as disclosed herein.

Such empirical studies are specifically designed and conducted, via means and methods which are well known and established in the art, to develop at least one overall formula for producing and manufacturing the optimized solution/suspension/slurry comprising this embodiment of the present invention.

The formula(s) developed from these studies is utilized to produce the opacifying, "solution/suspension/slurry" comprising this embodiment of the present invention, resulting in the creation of a functionally-optimized overall final product having individually-optimized ingredients which also function optimally as a whole, as disclosed in the present invention. This final product is then topically applied to the skin, onto a portion of the untreated hypodermic injection site, "a.", of FIG. 1., and is allowed to dry prior to the administration of an injection. This results in the deposition of an optimized, uniformly dense, uniformly thick, post-evaporation layer, onto the said injection site at area "c.", The said deposited layer consists of the said optimized sub-component ingredients comprising the said "non-volatile component" of the said final product. In the present embodiment, the said "non-volatile component" of the said final product, as specified in the said formula, is comprised of a mixture of optimized quantities of the sub-component ingredients comprising: $TiO_2$; dehydrated chitosan carboxyalkylamide; methylcellulose; and DSS, which are dissolved, and/or suspended in, and/or milled into a slurry with the said "volatile component". Following the topical application of the said final product to skin injection site area "c.", of FIG. 1., the said "volatile component", which, in this case, is comprised of an optimized percentage of isopropyl alcohol, rapidly and progressively evaporates from area "c.", thereby progressively depositing the said sub-component ingredient mixture, comprised of $TiO_2$, dehydrated chitosan carboxyalkylamide, methylcellulose, and DSS, onto area "c.", and thereby progressively forming the said uniformly dense, uniformly thick, post-evaporation deposited layer. The said deposited layer is considered to be optimized when it demonstrates a consistency of density, thickness, coloration, opacification and performance. When the said optimized solution/suspension/slurry comprising this embodiment of the present invention is mixed, the methylcellulose sub-component serves to suspend that fraction of each of the other sub-component ingredients which do not entirely dissolve in the said "volatile component" comprised of isopropyl alcohol. When the optimized solution/suspension/slurry comprising this embodiment of the present invention is applied to skin injection site area "c.", via the swab "f." of FIGS. 2, 3, and 4, the skin's surface tension at the said application site is reduced, via contact with the isopropyl alcohol and its DSS sub component, thereby facilitating consistency and uniformity in the deposition of the said deposited layer. The said layer is deposited onto the skin injection site area "c." of FIG. 1., and also serves to visually occlude any surface and sub-surface skin blemishes residing beneath area "c.".

Thus, when a hypodermic injection is administered through the said layer covering skin injection site area "c.", FIG. 1., and the needle is withdrawn from the skin, the $TiO_2$ and dehydrated chitosan carboxyalkylamide sub-components become visibly and progressively discolored by the blood/body fluids oozing from the needle's skin surface wound opening, "e.", thereby forming the discolored area "f.", while such fluids progressively ooze from the needle puncture skin surface wound opening, "e.", and spread outward. The oozing blood/body fluids also simultaneously and progressively react with the dehydrated chitosan carboxyalkylamide sub-component, to initiate the formation of a visible blood clot at the needle puncture skin surface wound opening, "e.", in addition to becoming progressively discolored along with the said $TiO_2$ sub-component at area "f." as previously cited, thereby further enhancing the visibility of the said skin surface wound opening, "e.".

The W/W ratios of the individual sub-component ingredients of the said "non-volatile component" to one another, and the W/V ratios of each of those ingredients to the volume of the said "volatile component", as described in one or more of the non-limiting examples disclosed under the above section titled "The Manufacture of the System of the Present Invention", are custom tailored by simply varying the ratios of the ingredients to one another until an optimally-performing post-evaporation deposited layer is obtained, following the application of one of the solutions/suspensions/slurries comprising this embodiment to a hypodermic injection site. Optimal performance of such deposited layers depends as much on the density and/or thickness of the said deposited layer, as it does on such ratios. Without the use of standardized formulas, such as one or more of the non-limiting examples disclosed under the above section titled "The Manufacture of the System of the Present Invention", variations in the above-cited W/W and/or W/V ratios of such examples would consequently result in variations in the densities of such post-evaporation deposited layers, which would degrade the performance and functional reliability thereof. This would be undesirable.

The optimal performance of the said deposited layer is therefore a function of its density and/or thickness, which, in turn, is a function of the presence of optimal quantities of each of its individual sub-component ingredients comprising the said layer, all in accordance with the said optimized formula derived from the use of the above-cited examples. It should be noted that excessive density and/or thickness of the said deposited layer can interfere with the visibility of the discoloration of the said deposited layer, which would otherwise form a visible ring around the said skin surface wound opening, "e.", in response to the oozing of body fluids from such a wound opening. The said optimization of the said deposited layer ensures that such excessive layer density and/or thickness does not occur. Means and methods for studying such compositions by simply varying the ratios of their ingredients, are easily performed by anyone skilled in the art, and such means are useable to achieve optimal performances for the deposited layers in each of the embodiments of the present invention.

It should be noted that the weight to volume relationships of the various ingredients of the various embodiments of the present invention can be individually calculated using the following simple equation, and that these relationships may vary from one embodiment to the next:

% W/V=grams of solute/100 milliliters TOTAL VOLUME of solution or suspension.

Numerous additional means and methods for conducting such studies and for obtaining results similar to those disclosed in the present invention are feasible, and are therefore also claimed as falling within the scope and intent of the present invention.

With regard to the "volatile component" of this embodiment of the present invention, the optimal percentage of isopropyl alcohol to be utilized in this formula is determined by empirically-based studies in which, for example, a number of individual, pathogen-culturing vessels, each containing appropriate culture media (including, for example, tissue cultures for virucidal studies) are maintained at a normal skin surface temperature of say 95-97 degrees F. and are each identically inoculated with a variety of targeted pathogens and then appropriately incubated. The pathogens growing in each of the individual culturing vessels are subjected to direct physical exposure to an individually-standardized variation of the said devised formula, the "volatile component" of each such variation being individually formulated to comprise a different percentage of, say, isopropyl alcohol, at, i.e. 70%, 71%, 72%, and 73%, etc., etc. The pathogens grown in each individual culturing vessel are exposed to one of the said variations of the said devised formula. In each case, the tested formula variation is allowed to evaporate immediately prior to evaluation. Each of the treated areas within each of the said culturing vessels is then immediately examined for pathogen mortality, which is then compared to the pathogen mortality observed in each of the other treated culturing vessels used in the series, in order to identify the optimal formula variation which has the greatest pathogen lethality in relation to time-of-exposure and percentage of alcohol content. When testing the said "volatile component" variations cited in the present example, the content comprising the tested "non-volatile component" sample in each of the said "volatile component" formula variations has previously been optimized and remains constant. In the present example of an empirically-based study, the devised formula which demonstrates the greatest pathogen lethality comprises the most optimized of the said devised and studied formula variations in relation to the pathogens selected for study. This optimized "volatile component" variation is therefore the one which should be utilized in manufacturing the solution/suspension/slurry comprising this embodiment of the present invention.

The formula comprising this first embodiment of the present invention represents the final outcome of such rudimentary empirical studies, which are designed and conducted to optimize both the selection and performance of each of the individual sub-component ingredients comprising its "volatile and non-volatile components", and the performance of the formulation as a whole. This optimized formula demonstrates the greatest intended level of performance, both for each of its individual sub-component ingredients, and for the formulation as a whole, and is therefore intended to be utilized, with or without further modification, in commercially manufacturing this embodiment of the present invention. This optimized formula is then extrapolated for large scale manufacture, and for packaging in a variety of formats, including the one cited herein, in FIGS. 2, 3, and 4. It is acknowledged: that numerous other means and methods for conducting such empirically-based studies exist; that such means and methods are well known in the art; that such means and methods may be employed by one skilled in the art, to achieve one or more optimal results for the disclosed invention; and, that all such other means and methods are to be included within the scope and intent of the present invention.

In addition to the foregoing, prior art discloses that some tints, dyes and/or colorants, such as Acriflavin (an Acridine dye), possess their own inherent antiseptic, and/or antimicrobial properties, and the above-cited studies are to be devised to include and take synergistic advantage of such properties by including such substances in the said studies and preferably in one or more formulations of the present invention. The inclusion and use of such tints, dyes and/or colorants in such optimized formulations of the present invention provides additional obvious health benefits to patients receiving injectable medicines. Therefore, their inclusion and use in formulating one or more of the variations of the said "solution/suspension/slurry" of the present invention is also intended to fall within the scope and intent of the present invention.

As specified in the above-cited, empirically-derived optimal formula utilized in this embodiment of the present invention, the formula-specified quantities of the individual sub-component ingredients comprising the said "non-volatile component" are suspended and/or dissolved in the formula-specified volume of the said "volatile component", thereby producing the "solution/suspension/slurry" comprising this embodiment of the present invention. In this embodiment of the present invention, the said optimized, "solution/suspension/slurry" is commercially manufactured in disposable, unit-of-use packaging, as illustrated in FIGS. 2 through 4, utilizing at least one of the packet assembly processes disclosed in the prior art, such as a hermetic sealing process, whereby the said optimized solution/suspension/slurry is applied to the said cloth or other sponge-like, absorbent fabric or fibrous patch or swab, "f.", in a precisely controlled and measured quantity sufficient to achieve saturation of the said patch "f.", which is then encapsulated and sealed between components "a." and "b." of FIG. 4, the sealing process being applied within area "c.", of components "a." and "b.", thereby forming a sealed, disposable packet containing the said solution/suspension/slurry-saturated patch, swab, or wipe, "f.". The sealed packet illustrated in FIG. 4 is then ready to be torn open, via tear slot "g.". The said packet is torn open at slot "g.", and the said saturated patch or swab, "f.", is physically removed from the said packet and is applied to an untreated area of human skin, "a.", at skin injection site area "c.", of FIG. 1., prior to the administration of a hypodermic injection. The calculated volume or weight of the said measured quantity of the said optimized, "solution/suspension/slurry" which saturates patch or swab "f." must be sufficient to adequately and uniformly coat the skin injection site area to which it will be applied and possibly re-applied.

The specific volume or weight of the said measured quantity of solution/suspension/slurry, which is required to effect the deposition of a functional post-evaporation layer comprised of the sub-component ingredients of the said “non-volatile component”, is also determined by simple, basic empirical study, via means which are well known in the art. When the said sealed packet illustrated in FIG. 4 is torn open and the said solution/suspension/slurry is applied to the said skin injection site area, “c.”, of FIG. 1, via the use of the said saturated patch or swab, “f.”, of FIG. 4., the said “volatile component” of the said applied solution/suspension/slurry quickly evaporates, thereby effecting the deposition of a post-evaporation layer or coating comprised of the sub-component ingredients of the said “non-volatile component”, onto the skin injection site area, “c.”, of FIG. 1. The said deposited layer or coating is dense enough to produce opacification of the underlying treated skin area, but is not too dense to interfere with the visibility of the physical reaction which occurs between the sub-component ingredients of said “non-volatile component” comprising the said deposited layer or coating, and minute quantities of the said oozing body fluids which will typically ooze from the skin surface wound opening, “e.”, of the needle puncture entry wound, “d.”, following the administration of an injection and the withdrawal of the hypodermic needle from the site of injection. Thus, the application of the said “solution/suspension/slurry” to a proposed skin injection site results in the formation of a dry or semi-dry, post-evaporation layer comprised of the said “non-volatile component” ingredients at the said skin injection site, the deposited layer having sufficient density to perform as disclosed herein.

In addition to addressing the above-cited issues related to improving the visibility of skin injection site puncture wounds, this embodiment of the present invention also addresses important health and safety issues associated with excessive injection site bleeding which often occurs in a number of patients. It is understood that excessive injection site bleeding further increases the potential for health care workers’ exposure to blood borne pathogens, and also increases the generation of bio-hazardous waste materials, both of which significantly increase the potential for the proliferation of blood borne diseases such as Hepatitis A, B, C, E, HIV, Meningitis, etc. As cited above, the present invention addresses these issues by adding one or more known blood coagulants, such as one or more of the chitosan derivatives, collagen, and possibly thrombin, etc., to the “solution/suspension/slurry” comprising the present invention.

Several criteria, including cost, should be considered when selecting one or more blood coagulants for inclusion in the formulation of this embodiment of the present invention. Primarily, as with each of the other ingredients which comprise this embodiment of the present invention, each of the said coagulants potentially considered for use in this embodiment is empirically studied within the context of this embodiment of the present invention, to determine its optimal concentration in relation to producing both the most robust clotting response and the fastest clotting time at a given post-injection puncture wound site. Combinations of two or more such coagulants are also empirically studied to determine if one or more of such combinations produces an optimal clotting response which is more robust and faster than that produced by any of the individual coagulants studied. The “robust” aspect of the said clotting response pertains to the rate of clot formation and the density of a formed clot.

Each of these coagulants and each possible combination of such coagulants is studied at various concentrations within a standardized volume or weight of the said “solution/suspension/slurry” comprising the present invention. For example, the materiel for conducting such studies may comprise a series of individual vessels, each containing an equal volume of an identical formulation comprising the “solution/suspension/slurry” of the present embodiment, minus its coagulant sub-component, which is separately added to each individual vessel, in a precise, yet different measured quantity, thereby allowing this group of such vessels to be comparatively evaluated in order to identify the coagulant quantity which demonstrates the greatest efficacy in terms of clotting response, each such individually-measured quantity being expressed as its own W/W and/or W/V ratio(s). The resultant coagulant-enhanced solution/suspension/slurry contained within each such vessel is studied to quantify its coagulating effects on the density of the clots it forms and on the clotting response time. The coagulant or combination of such coagulants which is identified through such studies as having both the highest clot density and the fastest clotting response time is then utilized in this formulation of this embodiment of the present invention and is added in the quantity representing its study-determined, optimal W/W and/or W/V ratio, thereby producing optimized coagulant performance in association with the use of the “solution/suspension/slurry” comprising this embodiment of the present invention.

Additional factors to be considered in evaluating coagulant clotting response in the context of the present invention include, but are not limited to:

the effects of blood type on the speed of post-injection clot formation and the density of the clots formed;

the effects of blood density/viscosity of each known blood type (as determined by the percentage of its water content, etc.), on the speed of post-injection clot formation and the density of the clots formed;

the effects of each known blood type’s intrinsic clotting factors on the speed of post-injection clot formation and the density of the clots formed;

the effects of the degree and rate of bleeding at the post-injection needle puncture wound opening on the speed of post-injection clot formation and the density of the clots formed, for each of the known blood types;

The said coagulant(s) or combinations thereof must also demonstrate no significant physical and/or chemical incompatibilities between themselves and between them and any or all of the other cited sub-component ingredients of the said "solution/suspension/slurry" comprising this embodiment of the present invention. The presence or absence of such physical and/or chemical incompatibilities is determined by: reviewing the existing literature pertaining to each of the individual sub-component ingredients; by reviewing the existing literature pertaining to known physical and chemical interactions occurring when such ingredients are mixed; and, if necessary, by conducting empirically-based studies or other studies which are designed to rule out such incompatibilities, utilizing means and methods which are well known and established in the art. It is acknowledged that one or more other known blood coagulants may be determined as being more effective than dehydrated chitosan carboxyalkylamide, consequent to their being subjected to study and evaluation in association with the above-cite four coagulant related criteria, or under similar criteria.

In the present embodiment, the blood coagulant dehydrated chitosan carboxyalkylamide is added to the above-cited formulation in an empirically-determined W/V or W/W ratio sufficient to effect robust and rapid coagulation of blood oozing from such post-injection needle puncture wounds. The said dehydrated chitosan carboxyalkylamide is evenly mixed with the said treated TiO2 powder, and this mixture is then uniformly suspended in the said "volatile component" utilizing a suspending agent, such as methylcellulose, the final mixture comprising the said "solution/suspension/slurry" of this embodiment of the present invention. When this formulation is applied to a skin injection site area, "c." of FIG. 1., a post-evaporation layer comprised of the said mixture of TiO2 and dehydrated chitosan carboxyalkylamide is deposited on the surface of the said injection site, thereby occluding any skin blemishes residing beneath it. When an injection is given at the said injection site, "c.", and the needle is withdrawn from the skin, any blood/body fluids which ooze from the said needle puncture entry wound "d.", of FIG. 1., will react with the TiO2 sub-component to increase the visibility of the said skin surface wound opening, "e.", of FIG. 1., and, any blood/body fluids which ooze from the said needle puncture entry wound, "d.", will also react with the said dehydrated chitosan carboxyalkylamide sub-component to effect the formation of a blood clot at the said skin surface wound opening, "e.", which will both reduce the said bleeding and further enhance the visibility of the said skin surface wound opening, "e.". This reduction in bleeding reduces the risk of exposure to blood borne pathogens for both the administrators of injectable medicines and for other persons who may come into contact with medical waste produced in controlling such bleeding. Dehydrated chitosan carboxyalkylamide is a compound which is well known in the art, and is commercially available in solid form, as a powder, or as a gel, which is formulated via means disclosed in prior art. It is also well known for having superior antimicrobial efficacy, and any bleeding which might occur from such needle puncture wounds would be subject to its antimicrobial effects, as well as to its coagulant effects.

The use of dehydrated chitosan carboxyalkylamide as a coagulant in the present context has additional medical benefits for patients receiving injectable medicines, namely: chitosan itself is known to possess antiviral properties, and when it combines with silver to form a complex, such a combination demonstrates additional antiviral, antibacterial and antifungal properties. These attributes are well known in the art and are disclosed in existing literature. Because of these attributes, the use of such a combination in the present invention also reduces the infectiousness of any blood/body fluids which ooze from post-injection needle puncture wounds, thereby further reducing the spread of blood-borne diseases in the context disclosed herein. In addition, some forms of silver, such as silver nitrate, are used medically to cauterize wounds and lesions, thereby adding the additional benefit of partial cauterization of needle puncture wounds when used in the context of the present invention.

While dehydrated chitosan carboxyalkylamide is cited as a preferred coagulant in this embodiment of the present invention, any known coagulant, or any combination of such known coagulants, which have been subjected to evaluation under the above-cited criteria, or similar criteria, and which have been found to be superior to dehydrated chitosan carboxyalkylamide, can be utilized to formulate additional variations of this embodiment of the present invention.

A second embodiment of the present invention is comprised of variations of the first embodiment wherein one or more pigments, such as Anthrapyrimidine Yellow (PY 108), and/or Isoindolone Yellow R (PY110), are added to or substituted for the said treated TiO2 powder cited above in the primary embodiment, thereby effecting the colorization of the "non-volatile component", of which the coagulant dehydrated chitosan carboxyalkylamide is an ingredient. The coloration of the said "non-volatile component" therefore stems from the colorization of the TiO2 and/or the dehydrated chitosan carboxyalkylamide. In any case, when the "solution/suspension/slurry" comprising the present embodiment is applied to a randomly-chosen hypodermic injection site, its "volatile component" evaporates, thereby depositing a uniformly dense and uniformly-pigmented layer or coating comprised of the said "non-volatile component", onto the surface of the said injection site as previously cited. This layer or coating serves to demarcate the outer boundary of the said injection site, and to effectively occlude or mask the visibility of any underlying skin blemishes, freckles, tattoos, or other skin markings which may reside beneath the said layer or coating.

In the present embodiment, the specific metric quantity of the pigment PY 108, or one or more other such compatible pigments which is required to produce an effectively dense, uniformly occlusive, uniformly-pigmented post-evaporation layer or coating at such an injection site, is determined by empirical experimentations which are designed and performed to identify specific optimal W/W relationships between each of the ingredients comprising the said "non-volatile component", and to identify specific optimal W/V relationships between each of the ingredients comprising the said "non-volatile component" and the said "volatile component". The outcomes of such experimentations comprise specific quantitative values for each of the said ingredients, the combination of which represents an optimized formula for the said "solution/suspension/slurry" comprising this embodiment of the present invention. The said optimized formula is then extrapolated for large-scale manufacturing, and is incorporated into unit-of-use packaging such as the disposable packet illustrated in FIGS. 2-4. The patch or wipe, "f.", contained in such packaging is saturated with a small volume, eg. 1 ml to 1.5 ml, of the said optimized "solution/suspension/slurry", which, when applied to a randomly-chosen hypodermic injection site, effects the deposition of the said layer or coating which is optimized for density and uniformity of coloration. The designing and performance of such empirical experimentations, for purposes of obtaining specific quantitative values for each of the ingredients comprising the said optimized formula, are uncomplicated and easily fall within the capabilities of those skilled in the relevant art.

The colorized, powdered dehydrated chitosan carboxyalkylamide variation of the present embodiment functionally performs as:

a pigmented contrast medium for demarcating the outer boundaries of randomly-chosen hypodermic injection sites and for determining the continuity-of-sanitization of such demarcated injection sites;

an opacifying agent which visually conceals or masks skin surface blemishes residing beneath such demarcated injection sites;

a contrast medium for detecting the surface openings of hypodermic needle puncture wounds inflicted within the boundaries of such demarcated injection sites; and, as a coagulant which reduces bleeding from such wound openings, while forming a visible clot which also improves the visibility of the said needle puncture wound prior to its bandaging.

This optimized "solution/suspension/slurry", when applied to human skin, results in the deposition of a post-evaporation layer which is dense enough to produce both opacification of the underlying treated skin area and robust clotting at the needle puncture wound opening, but which is not too dense to interfere with the visibility of the discoloration and clotting reaction occurring between the said deposited layer or coating and the minute quantities of blood and body fluids which normally ooze from such wounds. When this formulation is applied to human skin, it forms a deposited post-evaporation layer comprised of pigment/tint/dye/colorant-enhanced dehydrated chitosan carboxyalkylamide which occludes, conceals, or masks the visibility of any blemishes or other markings which may reside on the surface of the skin directly beneath the said treated skin injection site area, the degree of such blemish occlusion ranging from translucent to opaque. In this embodiment, the said mixture of blood and body fluids oozing from such a needle puncture wound coagulates, by process of muco-adhesion, when coming into contact with the said deposited layer. The presence of at least one surfactant, such as DSS, in the said deposited layer, enhances this process, and functions as an adjunct by increasing the degree of discoloration of the said deposited layer adjacent to the said needle puncture wound, thereby further improving wound visibility. This improved surface discoloration at the needle puncture wound site, when combined with the clot formed by muco-adhesion, significantly augments the visibility and location of the said wound site. The contrast in coloration between the said deposited layer and the coagulated blood/body fluids is sufficiently visible to the administrator of such an injection, to allow for the accurate identification and bandaging of the said needle puncture wound, as before. The said deposited layer will also reduce excessive bleeding from the said needle puncture wound. If the coloration of the said dehydrated chitosan carboxyalkylamide obtained by using Anthrapyrimidine Yellow (PY 108), or Isoindolone Yellow R (PY110) is inadequate within the context of the present invention, then Acriflavin or another pigment/tinting agent is substituted, in an empirically-determined, optimized quantity which will sufficiently colorize the dehydrated chitosan carboxyalkylamide, thereby enabling the said deposited layer to perform as cited herein.

In a third embodiment of the present invention, the "non-volatile component" ingredients previously cited are dissolved and/or suspended in an antimicrobial, semi-solid gel comprised of a mixture of gelled alcohol and one or more other antimicrobial compounds, such as chlorhexidine gluconate, which can be applied to a hypodermic injection site via a patch or utilizing a multi-use container similar to those used in roll-on deodorants or gel-dispensing deodorants. The design of such packaging must include means for completely covering the applicator surface with the said gel component, in order to ensure that live microorganisms will not contaminate the said applicator surface, in order to prevent their physical transfer from one patient to the next. Any such modifications of the present invention in terms of the formulation of such gels and any delivery mechanisms designed to apply them to an injection site, are acknowledged and claimed as falling within the scope and intent of the present invention.

In a fourth embodiment of the present invention, the pigment/tint/dye/colorant-enhanced, body-fluid-reactive, blood coagulant-enhanced, skin injection site sanitizing/sterilizing solutions/suspensions/slurries comprising its first, second and fourth embodiments, are reformulated, yet are utilized in the same manner as disclosed therein. Each of these embodiments is reformulated by replacing their cited pigments/tints/dyes/colorants with pigments/tints/dyes/colorants/paints, etc. which are capable of fluorescing when exposed to the ultraviolet (UV) and/or infrared (IR) spectra of radiation. Such fluorescing pigments/tints/dyes/colorants/paints are amply disclosed in the literature of pertinent prior art, and are commercially and widely available. Fluorescein is an example but is unstable in aqueous solutions. A wide range of UV fluorescing pigments, including but limited to Long Wave UV Inorganic, Long Wave Organic, and Short Wave Organic pigments, Water-Based Clear Black Light Paints, and Invisible (White to Color) Water-Based Black Light Paints, all in a variety of colors, are commercially available through internet sources such as via the Risk Reactor Company's website www.riskreactor.com. The application and use of such substances within the context of the present invention is claimed as falling within the scope and intent thereof. In the context of the present invention, the use of such invisible pigments is preferable, for obvious cosmetic and practical reasons, although the use of other such pigments and dyes which are visible, is not precluded. In the context of the present invention, the use of such fluorescing pigments is coupled with the use of a proximate UV light source, which is used to irradiate a skin injection site treated with the said solutions/suspensions/slurries comprising this embodiment of the present invention. Such a UV light source may be free-standing, or may be designed as an attachment to a hypodermic injection device, and its design and use as such, is acknowledged and claimed as falling within the scope and intent of the present invention.

Some of the pigments or dyes which fluoresce when irradiated with IR radiation, such as those in the Cyanine class of dyes, and which are currently used in protein, antibody, nucleic acid, and other biomolecular labeling applications, may also be adaptable for use in place of, or in combination with the said UV fluorescing pigments, and in the same or similar manner as disclosed in this embodiment of the present invention. In the context of the present invention, the use of such IR fluorescing pigments is coupled with the use of a proximate IR light source, which is used to irradiate a skin injection site treated with the said solutions/suspensions/slurries comprising this embodiment of the present invention. Such an IR light source may be free-standing, or may be designed as an attachment to a hypodermic injection device, and its design and use as such, is also claimed as falling within the scope and intent of the present invention.

In a fifth embodiment of the present invention, a locally-acting, topical anesthetic is added to the "non-volatile component" of one or more of the previously-cited embodiments, in order to decrease the discomfort associated with the piercing of the skin by a hypodermic needle, accupuncture needle, or other such instruments. One or more locally-acting topical anesthetics such as benzocaine, lidocaine, dibucaine, etc., is added to one or more of the "non-volatile component" mixtures of the above-cited embodiments, in sufficient quantity to effect localized anesthesia of the skin area on which the said "non-volatile components" have been deposited. The optimal quantities of such topical anesthetics required to effect such local anesthesia are determined by empirical experimentations which are easily performed by those skilled in the art. Additional empirical experimentations are performed to determine physical and chemical compatibility of each of the studied anesthetics with each of the other ingredients comprising one or more of the above-cited "non-volatile components", such experimentations being easily performed by those skilled in the art. The outcome of the cited empirical experimentations identifies the optimal anesthetic(s) and the optimal quantity or quantities of the so-identified optimal anesthetic(s), in relation to their desirable physical and chemical compatibilities with the other ingredients comprising the said "non-volatile components". The local anesthetic(s) thus identified and measured, are added to the said other ingredients comprising one or more of the said "non-volatile components" of one or more of the cited embodiments of the present invention, thereby comprising this fifth embodiment.

In a sixth embodiment of the present invention, a non-limiting example of an aerosol is disclosed, in which the volatile component ingredient is comprised of an anesthetizing refrigerant such as Ethyl Chloride, to which is added, by dissolution and/or suspension, one or more of the non-volatile component ingredients comprising one or more of the non-volatile ingredients of the previous embodiments, and includes the substitution of one or more additional dyes or pigments for those in the previous embodiments. Preferably, the said substituted dyes or pigments have physical and/or chemical characteristics and properties functionally similar to those utilized in the previous embodiments, which likewise enhance coagulation and needle puncture wound visibility.

It should be noted that in each of the following embodiment variations, an anesthetizing refrigerant such as Ethyl Chloride functions as: a topical refrigerant/anesthetic; a solvent for the non-volatile ingredients; a sanitizing/sterilizing agent for injection site skin surfaces; and, as a vehicle for physically delivering all of the component ingredients to a selected injection site.

In one, non-limiting variation of the present embodiment, the pigments Arylide Yellows G and 10G are dissolved in the volatile component, while the micro-particulate pigment Yellow Ochre is combined with a suspending agent and is then treated with a surfactant prior to being suspended or stabilized in the said volatile component. In a second, non-limiting variation, the micro-particulate pigment Yellow Ochre alone is combined with a suspending agent and is then treated with a surfactant prior to being suspended or stabilized in the said volatile component. The color yellow is preferred because its wavelengths are the most visible to the human eye. The volatile Ethyl Chloride component performs several functions. It serves as a sanitizing agent, which also rapidly evaporates to produce temporary localized cryo-anesthesia, while also serving as a vehicle for the dissolution and/or suspension of the said non volatile component ingredients, in addition to serving as a vehicle for their delivery to a selected injection site.

In other, non-limiting variations of the present embodiment, one or more dyes or pigments, such as a mixture of Arylide Yellow G and Arylide Yellow 10G, are added to and dissolved or suspended in the Ethyl Chloride component. Micro-particulate Yellow Ochre, alone or in combination with either a micro-particulate polysaccharide such as micro-particulated, dehydrated chitosan carboxyalkylamide, or micro-particulate titanium dioxide, any or all of which probably require pre-treatment with a surfactant such as Dioctyl Sodium Sulfosuccinate (DSS) and/or a stabilizing agent such as Polyvinylpyrrolidone (PVP K-30) in powdered form. One or more combinations of these non-volatile components is mechanically blended with the DSS and PVP before being gradually blended into the above-cited Ethyl Chloride/Arylide pigment solution. The particle sizes of each of the non-soluble non-volatile ingredients, and the concentrations of each of the ingredients comprising the resultant mixture should be such that it's fluidity characteristics are retained sufficiently to allow for its unhindered expulsion through the non-clogging aperture of a metered dispensing device. The said resultant mixture must also retain the ability to form a viable post-evaporation deposited layer comprised of its non-volatile ingredients, onto skin area. When the combined solution/suspension comprising one or more of the variations of the present embodiment is sprayed onto a randomly-chosen hypodermic injection site, its' rapidly-evaporating "volatile component" cryo-anesthetizes the underlying skin, while its "non-volatile component" forms a uniformly dense and uniformly-pigmented barrier layer or coating on the skin surface of the said injection.

It should be noted that prior to the combining of any of the above cited component ingredients in formulating each of the preferred embodiments of the present invention, the literature pertaining to various possible combinations of all such ingredients should be studied by one skilled in the art, to ascertain whether or not any chemical and/or physical incompatibilities exist between the various said component ingredients, which would interfere with the functional performance of the present invention as disclosed herein. If any such incompatibilities are found to exist, then other, functionally-similar or functionally-equivalent component ingredients can be substituted for those having such incompatibilities, and such substitutions are permissible within the context of the present invention and all of its embodiments, and as such, are claimed as falling within the scope and intent of the present invention.

It should also be noted that it is not within the scope and intent of the present invention, to necessarily recite specific details pertaining to any or all of the empirical experimentations/studies cited in the present disclosure, above and beyond the example given, since these experimentations/studies can easily be performed by one skilled in the art, and can yield a large number of, and a wide variety of outcomes, and, because the outcomes of such experimentations/studies are easily achievable within the scope and context of the present invention.

Those skilled in the art can readily practice the present invention without undue experimentation by varying the measured quantities of one or more of their component ingredients;

changing one or more of the relationships between one or more of their component ingredients;

substituting one or more other, but functionally-similar or functionally-equivalent component ingredients for one or more of the component ingredients comprising the present invention, in order to formulate additional embodiments thereof;

varying the measured quantities of one or more of such substituted component ingredients;

combining one or more of the features or attributes, of which such additional embodiments are comprised, with one or more features comprising other such additional embodiments, in order to derive one or more variations of such additional embodiments.

Within the context of the present invention, the pigment/tint fraction of the "non-volatile component" of the said "solution/suspension/slurry" comprising the present invention, may itself also be comprised of one or more of the substances listed below, and/or one or more of the substances which comprise the categories of other pigments, dyes or colorants listed below, yet is not limited to the utilization of only one or more of those listed substances. One or more of such substances may be utilized to contribute to the colorization and/or opacification of the said post-evaporation deposited layer comprising the said "non-volatile component" of the present invention, as disclosed herein, and such substances may also physically and/or chemically react with any or all of the said body fluids oozing from the said hypodermic needle puncture wounds. The physical and chemical attributes of each of the following listed substances, as well as those of any other such substances whose use can be contemplated but which are not specifically cited herein, are to be thoroughly reviewed by one skilled in the art, to determine their appropriateness for use in the context of the present invention, in order to rule out those substances which are physically and/or chemically incompatible with the other ingredients comprising the present invention, as well as to rule out those substances which present an unacceptable level of toxicity, again within the context of the present invention. It should be noted that the color yellow is the easiest color for the human eye to see, because most of the cones in the eye are sensitive to it. Therefore, the colorants of choice, for use within the context of the present invention, are those which impart yellow coloration to the said deposited layer covering hypodermic injection sites treated with the present invention. It should also be noted that if a Red colorant is used, its coloration should be such that it does not interfere with the visibility of blood/body fluids oozing from post-injection, hypodermic needle puncture wounds. Colorants which also possess additional, synergistically-advantageous antiviral, antibacterial, and/or other anti-microbial attributes, such as Acriflavin, are also to be considered for possible use in context with the present invention. It is noted that the list of pigments cited below is by no means complete, and that some of the listed pigments may be more appropriate for use than others, within the context of the present disclosure, and that no pigments are completely non-toxic in dry powder form. Other suitable pigments, dyes or colorants not cited herein are claimed as falling within the scope and intent of the present invention. Manufacturing considerations should include utilizing those substances which are least toxic with regard to worker exposure in the workplace, in order to avoid potential safety violations and their associated restrictions and fines.

Yellow Ochre PY ASTM 1 is an inorganic natural iron oxide—generally considered to be non-toxic, but some variants may contain manganese (considered toxic) but exposure to its dust is extremely limited in the present application. It should be noted that the color yellow is the easiest color for the human eye to see, because most of the cones in the eye are sensitive to it. It is also suitable for use as a watercolor dye.

Anthrapyrimidine Yellow (PY 108) is non-toxic, transparent, and is bright yellow in color.

Isoindolone Yellow R (PY 110) ASTM 1 is non-toxic and is bright reddish yellow in color.

Pthalo Blue PB 15 & 16 ASTM 1, and Pthalo Green PG 7 ASTM 1, are copper-containing, organic synthetic Pthalocyanines which exhibit only slight toxicity, the levels of which are insufficient to exclude them from being utilized in formulations of the present invention. They are also relatively safe for inclusion in formulations of the present invention, because adult patients receiving hypodermic injections through skin which has been treated with such formulations will have only very limited exposure to them. Their use, within the context of the present invention, may also prove advantageous because of their overpowering coloration, thereby both improving the visibility of the hypodermic injection sites to which they have been applied, and by effectively obscuring any naturally-occurring skin blemishes residing beneath such treated skin areas, as disclosed herein.

Green Earth PG 23 ASTM 1 is comprised of inorganic ferrous silicates with aluminum and magnesium, and is considered as being non-toxic, but provides weak pigmentation, which may be a desirable attribute in some formulations of the present invention.

Pyrrole Red PR 254 ASTM 1 is an organic synthetic Pyrrole which is considered non-toxic, but causes permanent coloration and staining, which therefore may not be suitable for application to human skin within the context of the present disclosure.

Alizarin Crimson PR 83 ASTM 111 is an organic synthetic Anthraquinone, which is less light fast than an ASTM 1, making it too impermanent to be used in artwork, but making its use as a colorant possibly desirable within the context of the present invention.

Quinacridone Red Y (PR 192) is an organic synthetic Quinacridone ASTM 1, which produces bright, transparent clear colors, which may be too permanent for use in formulations of the present invention, without adequate dilution.

Napthol Red PR 17 ASTM 111 is an organic synthetic monoazo compound, which is barely light fast (barely ASTM classified), and will fade in tints. It is relatively inexpensive and is not considered toxic, thereby making it potentially useable as a colorant in formulations of the present invention, if rapidly fading coloration of the said deposited layer is desirable.

Common Food Coloring Agents—alone or in various combinations, can also serve as tinting agents in formulations of the present invention. These agents are non-toxic, and are soluble in both alcohols and water. They are removable from patients' skin, by mildly scrubbing with soap and water, and may not permanently stain the fabric of patients' clothing. An example of a useable dye-to-reagent ratio, using FD&C Blue 1 as the tinting agent fraction of the said "non-volatile component", and 70% Isopropyl Alcohol as the said reagent or "volatile component", is comprised of approximately 18 drops of the said tinting agent which is added to the said "non-volatile component", which is then dissolved and/or suspended in approximately 15 milliliters of the said reagent or volatile component. Each patch is impregnated with approximately 0.4 milliliters of such a mixture, and is encapsulated in a sealed packet, which is then ready to be opened and used as disclosed herein. The application of the said mixture to a hypodermic injection site via the said patch will effect the formation of a post-evaporation deposited layer having faint blue coloration which is sufficient to demarcate the said injection site and to partially occlude the skin blemishes residing beneath it. It should be noted that it is known in the art, the some Yellow food colorings can produce allergic reactions and their use should therefore be avoided in the present invention.

Other colorant substances and colorants useful in the practice of the present invention, include but are not limited:
triarylmethane dyes
indigo dyes
xanthine dyes
quinophthalone
anthraquinone dyes
quinoline yellow (E104)
patent blue V (E131)
brilliant green BS (E142)
various water color pigments (such as the Yellow Ochre PY ASTM 1)
fluorescein, or other UV fluorescing dyes
carbocyanine dyes (capable of fluorescing in the visible IR spectrum of ~400-650 nm)

It should also be noted that medium toxicity pigments may be carcinogenic, including those which contain heavy metals such as Cobalt, Titanium and Umber (Manganese). High toxicity pigments are those which contain Lead and Arsenic. Obviously, the present disclosure does not recommend any high toxicity pigments for inclusion in any of the formulations comprising the present invention.

DETAILED EXPLANATION OF THE DRAWINGS

Standards pertaining to the administration of hypodermic injections require the topical application of a sanitizing/sterilizing agent to any areas of skin intended for use as injection sites, in order to prevent infectious microorganisms from being introduced via that route. The following detailed descriptions and explanations of FIGS. 1 through 5b entail an example of the creation, manufacture, physical performance, and the practical and commercial application of a preferred embodiment of the present invention, explaining the components of, and the assembly of, an individually-sealed, disposable packet, containing a topically-applied, disposable patch, swab, or wipe which has been saturated with at least one of the said solutions/suspensions/slurries comprising the present invention, and detailing its ultimate application to a human skin hypodermic injection site and its performance during and after its application thereto.

FIG. 1. illustrates an exposed, un-sanitized area of human skin, "a.", which covers, for example, the deltoid muscle of the upper arm, and which has been selected as a general hypodermic injection site. The sealed, disposable packet illustrated in FIG. 4., is torn open at slot "g.", and the disposable, fluid-saturated fabric or sponge-like patch or swab, "f." is removed therefrom and is directly applied onto skin injection site area, "c.", which is located within area "a.". Swab "f." is saturated with at least one of the disclosed solutions/suspensions/slurries comprising the present invention, some of which is physically transferred to skin injection site area "c." when swab "f." is applied thereto. As disclosed herein, the said transferred solution/suspension/slurry is comprised of "volatile and non-volatile components", and sanitizes/sterilizes the skin injection site to which it is applied. The "volatile component" of the said transferred solution/suspension/slurry rapidly evaporates from the surface of the said skin injection site area, "c.", leaving behind a visible, post-evaporation layer or coating which is comprised of the said solution/suspension/slurry's "non-volatile component", the ingredients of which are deposited onto the skin surface at injection site "c." consequent to such evaporation. The said layer or coating is relatively thin and its coloration can be opaque or translucent. This deposited layer or coating physically isolates the treated skin injection site area "c." from its local environment; maintains its underlying skin surface in a sanitized/sterilized state; and, renders it highly visible in contrast to the surrounding area of the untreated skin surface area "a.", while visually obscuring or reducing the visibility of any skin blemishes residing within the boundary of, and beneath the area of skin injection site area "c.".

The various ingredients comprising the said deposited layer or coating effect the visual demarcation of the treated skin injection site area, "c.", which enables an administrator of an injection to distinguish the treated area of skin, "c.", from the untreated area of skin, "a." The boundary, "b.", separates the said treated area of skin, "c.", from the untreated area of skin, "a.". FIG. 1 also illustrates the location of the skin surface wound opening, "e.", in association with its corresponding, post-injection, hypodermic needle puncture entry wound, "d.", from which various body fluids, including blood, will ooze, following the withdrawal of the hypodermic needle from the said needle puncture entry wound, "d.", within skin injection site area, "c.".

When a hypodermic injection is given within the boundaries of the said coated skin injection site area "c.", of FIG. 1., and the needle is withdrawn therefrom, the said blood/body fluids commence to progressively ooze and spread outward from the said skin surface wound opening, "e.", and progressively react, physically and/or chemically, with one or more of the ingredients comprising the said deposited layer or coating which covers the said skin injection site area, "c.". Such progressively-occurring reactions between the said layer or coating and the said oozing blood/body fluids produce a progressively-expanding, discolored, roughly circular pattern, "f.", which encircles the said skin surface wound opening, "e.", within area, "c.", wherein "f." represents the discolored area adjacent to, and inwardly bordering on the said skin surface wound opening, "e.". The progressively-expanding, discolored area, "f.", within area "c.", forms in response to the progressive exposure of its segment of the said deposited layer or coating, to the said blood/body fluids oozing outwardly from the said skin surface wound opening, "e.", of the said needle puncture entry wound, "d.". The discolored area, "f.", stands out in stark contrast to the coloration of the remainder of the said deposited layer or coating which covers area "c.", thereby rendering the said skin surface wound opening, "e.", of the said needle puncture entry wound, "d.", obviously visible to the administrator of the injection.

The composition of the said deposited layer or coating is comprised of at least two ingredients as follows: at least one opacifying pigment, tint, colorant, or dye, combined with at least one blood coagulant, as cited in one or more of the embodiments of the present invention. Each of the ingredients comprising the said layer reacts in its own way, when physically exposed to the said oozing blood/body fluids as follows: The pigment component of the said deposited layer or coating physically reacts by changing color as it adsorbs some of the said oozing blood/body fluids to which it becomes progressively exposed, while the coagulant component of the said layer or coating responds to such exposure to the said oozing blood/body fluids, by forming a visible blood clot at the site of, or proximate to, the said skin surface wound opening, "e.". The combined effects of these reactions produce a profound, visually-discernable contrast in coloration which distinguishes the area surrounding and adjacent to skin surface wound opening, "e." from the unaffected, remaining area of the said deposited layer at "c.", thereby rendering the said skin surface wound opening, "e.", and its associated needle puncture entry wound, "d.", obviously visible within area, "c.". In addition to further enhancing the visibility of the said wound opening, "e.", the formation of such blood clots also reduces the generation of infectious medical waste consequent to the hypodermic injection of vaccines and medicines, by reducing bleeding from such wounds.

FIG. 2. illustrates a two dimensional view of the individual components comprising one of the possible embodiments of the present invention, showing the unassembled individual parts of a disposable packet for containing the disposable, fabric or sponge-like patch, swab, or wipe, "f.", including a left panel, "a.", a right panel, "b.", and an absorbent or adsorbent fabric or sponge-like patch, swab, or wipe, "f.", which is saturated with the "solution/suspension/slurry" comprising the present invention. Panels "a." and "b." are each viewed from an interior-facing aspect, and are comprised of aluminized, polymer-coated paper or other material having functionally-similar properties, each such panel having an exterior-facing and an interior-facing surface. FIGS. 2 and 3 illustrate the interior-facing surfaces of both panels "a." and "b.", each of which have been coated with a heat-reactive, reagent-insoluble polymer or other material having functionally similar properties. The areas "c." of both panels "a." and "b.", each bordering on interior boundary "d.", indicate where heat or other sealing processes are to be applied during the physical assembly of components "a.", "b." and "f.", thereby forming a sealed, disposable packet containing component "f". The areas marked "e." on panels "a." and "b." of FIGS. 2 and 3 illustrate the areas on panels "a." and "b." where no heat or other sealing processes are to be applied.

FIG. 3. illustrates the pre-assembly placement of the said component "f." of FIG. 2, within the said boundaries "d.", and between and within the said areas "e." of the said panels "a." and "b." It is understood that the said polymer-coated surfaces of panels "a." and "b." are positioned in geometrically-aligned, physical contact with each other, and that component "f." is placed within the said boundaries "d.", and between and within areas "e." prior to the application of at least one sealing process, such as heat, to areas "c." during the assembly and sealing of the said disposable packet. Processes for sealing such disposable packets are well known and are amply described in the prior art, and their application and use in the commercial manufacturing of one or more of the embodiments of the present invention is claimed as falling within the scope and intent thereof.

FIG. 4. illustrates the assembled and sealed components comprising FIGS. 2 and 3, wherein the said panels "a." and "b." have been placed in opposing, geometrically-aligned, physical contact with each other and have been fused together by heat or other sealing processes at area "c.", thereby producing an airtight, sealed, disposable packet which encapsulates the "solution/suspension/slurry"-impregnated fabric or sponge-like patch or swab "f." in a reagent-insoluble, vapor-impregnable plastic barrier. FIG. 4 also illustrates the inclusion of a tear slot, "g." to facilitate the tearing open of the said sealed packet prior to the application of the fluid/slurry-saturated fabric or sponge-like patch or swab "f." to a hypodermic skin injection site. The processes used in the manufacture and sealing of such disposable packets are well known in the prior art, and produce an assembled product commonly known as a "wipe" or "swab", which outwardly resembles the so-called diabetic "alcohol swabs, or wipes" of the prior art. The administrator of an injection: tears open the said sealed packet at slot "g."; removes the said fluid/slurry-saturated patch or swab, "f." therefrom; applies the said patch or swab, "f." to area "c." of FIG. 1, thereby transferring the said "solution/suspension/slurry" comprising the present invention onto the surface of the said patient's skin injection site at area "c." of FIG. 1.; and, visually examines the post-evaporation, pigmented or tinted layer or coating deposited onto the said injection site at area "c.", to ensure its continuity of coloration, prior to administering a hypodermic injection at the said coated injection site.

FIG. 5.a. illustrates a cross sectional view taken from a frontal aspect, of a container and dispensing device used for topically applying a metered volume of at least one of the solutions/suspensions comprising the sixth embodiment of the present invention onto a hypodermic injection site. FIG. 5.b. illustrates the container and device of FIG. 5.a., which has been rotated 90 degrees counterclockwise on its vertical axis, and further illustrates the spraying of a metered volume of at least one of the solutions/suspensions comprising the present invention onto skin area, "a.", thereby forming the said post-evaporation deposited layer, "c.", covering part of the deltoid area of upper arm, "b.". The components common to both FIG. 5.a. and FIG. 5.b. are comprised of a dose metering valve, "d."; valve supply tube, "e."; valve actuator at rest, "f."; fluid ejection tube, "g."; fluid ejection tube aperture, "h."; aperture expansion chamber, "i."; expansion nozzle, "j."; metering valve cup seal, "k", which seats valve, "d.", thereby sealing container, "l.". Component "m." represents one of the said solutions/suspensions which are sealed within container, "l.". Component "n." represents the pressurized chamber which exerts expansive force onto component, "m.". Component "o." of FIG. 5.b., represents the valve actuator depressed in a downward direction, thereby ejecting a conically-shaped spray pattern which deposits the said solution/suspension in a circular pattern onto skin surface, "a.". The volatile component evaporates rapidly, thereby anesthetizing the skin beneath it, while forming the said post-evaporation layer, "c." comprised of the said non-volatile components. The expansion nozzle is positioned approximately 7.5 centimeters from the injection site target area, "a." prior to pressing the said valve actuator.

I claim:

1. A method for depositing a layer or coating that demarcates a hypodermic injection site on the skin of a subject prior to the injection of an injectable medicine at the hypodermic injection site, the method comprising demarcating the hypodermic injection site by topically administering a composition to the hypodermic injection site on the skin of the subject prior to said injection, the composition consisting of 1% w/v to 70% w/v of the visibility enhancer titanium dioxide ($TiO_2$);

1% w/v to 5% w/v of at least one sanitizer selected from the group consisting of chlorhexidine gluconate, isopropyl alcohol, and ethyl alcohol;

20% w/v to 70% w/v of the coagulant chitosan;

1% w/v to 20% w/v methycellulose; and, 0.1% w/v to 10% w/v dioctyl sodium sulfosuccinate or docusate sodium.

2. The method of claim 1 wherein said composition is applied to the injection site as a suspension.

\* \* \* \* \*